US012171879B2

(12) United States Patent
Traverso et al.

(10) Patent No.: US 12,171,879 B2
(45) Date of Patent: Dec. 24, 2024

(54) ARTICLES AND METHODS FOR ADMINISTRATION OF THERAPEUTIC AGENTS

(71) Applicants: Massachusetts Institute of Technology, Cambridge, MA (US); The Brigham and Women's Hospital, Inc., Boston, MA (US)

(72) Inventors: Carlo Giovanni Traverso, Newton, MA (US); Joshua Korzenik, Waban, MA (US); Robert S. Langer, Newton, MA (US); Christoph Winfried Johannes Steiger, Cambridge, MA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 17/569,881

(22) Filed: Jan. 6, 2022

(65) Prior Publication Data
US 2022/0202721 A1 Jun. 30, 2022

Related U.S. Application Data

(63) Continuation of application No. 16/991,536, filed on Aug. 12, 2020, now abandoned.

(60) Provisional application No. 62/885,450, filed on Aug. 12, 2019.

(51) Int. Cl.
*A61K 9/20* (2006.01)
*A61K 9/28* (2006.01)
*A61K 9/48* (2006.01)

(52) U.S. Cl.
CPC .......... *A61K 9/2054* (2013.01); *A61K 9/2013* (2013.01); *A61K 9/2846* (2013.01); *A61K 9/2866* (2013.01); *A61K 9/4858* (2013.01); *A61K 9/4866* (2013.01); *A61K 9/4891* (2013.01)

(58) Field of Classification Search
CPC .. A61K 9/2054; A61K 9/2013; A61K 9/2846; A61K 9/2866; A61K 9/4858; A61K 9/4866; A61K 9/4891
See application file for complete search history.

(56) References Cited

U.S. PATENT DOCUMENTS

| | | |
|---|---|---|
| 4,579,730 A | 4/1986 | Kidron et al. |
| 5,108,758 A | 4/1992 | Allwood et al. |
| 5,156,850 A | 10/1992 | Wong et al. |
| 5,171,580 A | 12/1992 | Iamartino et al. |
| 5,302,398 A | 4/1994 | Egidio et al. |
| 5,472,710 A | 12/1995 | Klokkers-Bethke et al. |
| 5,510,114 A * | 4/1996 | Borella ............ A61K 9/5084 514/774 |
| 5,514,663 A | 5/1996 | Mandel |
| 5,631,022 A | 5/1997 | Mandel et al. |
| 5,637,319 A | 6/1997 | Takada |
| 5,651,983 A | 7/1997 | Kelm et al. |
| 5,656,290 A | 8/1997 | Kelm et al. |
| 5,670,158 A | 9/1997 | Davis et al. |
| 5,686,105 A | 11/1997 | Kelm et al. |
| 5,840,332 A | 11/1998 | Lerner et al. |
| 5,843,479 A | 12/1998 | Kelm et al. |
| 5,846,983 A | 12/1998 | Sandborn et al. |
| 5,866,619 A | 2/1999 | Sintov et al. |
| 5,900,252 A | 5/1999 | Calanchi et al. |
| 5,914,132 A | 6/1999 | Kelm et al. |

(Continued)

FOREIGN PATENT DOCUMENTS

| | | |
|---|---|---|
| EP | 0 508 312 A1 | 10/1992 |
| EP | 0 572 942 B1 | 4/1997 |

(Continued)

OTHER PUBLICATIONS

Mikov et al., Pharmacology of Bile Acids and their Derivatives: Absorption Promoters and Therapeutic Agents. European Journal of Drug Metabolism and Pharmacokinetics 2006, 31(3):237-251. (Year: 2006).*
Hofmann et al., Bile Acids: Chemistry, Pathochemistry, Biology, Pathobiology, and Therapeutics. Cell. Mol. Life Sci. 2008, 65:2461-2483. (Year: 2008).*
Hofmann. Bile acids as drugs: principles, mechanisms of action and formulations. Ital J Gastroenterol. 1995, 27(2):106-113 (Abstract). (Year: 1995).*
Maderuelo et al. Enteric coating of oral solid dosage forms as a tool to improve drug bioavailability. European Journal of Pharmaceutical Sciences (2019), 138:1-15. (Year: 2019).*
International Search Report and Written Opinion for International Application No. PCT/US20/45987, mailed Nov. 18, 2020.

(Continued)

*Primary Examiner* — Robert A Wax
*Assistant Examiner* — Olga V. Tcherkasskaya
(74) *Attorney, Agent, or Firm* — Wolf, Greenfield & Sacks, P.C.

(57) ABSTRACT

Articles and methods for delivering a therapeutic agent to a subject are described. These articles and methods may be useful, in some cases, for the delivery of therapeutic agents to the colon of a subject. In some embodiments, an article is configured to release a secretion inducing agent e.g., to stimulate the release of intestinal fluids. The article, in some embodiments, comprises a therapeutic agent such that the stimulated release of intestinal fluid increases the amount of therapeutic agent available for absorption by the colon. For example, in some embodiments, the articles and methods described herein advantageously promote increased absorption of therapeutic agents in subjects as compared to traditionally administered therapeutic agents without additional components such as a secretion inducing agent. In some embodiments, articles and methods described herein may increase the motility of the colon of a subject. The increase in contractions and movement of fluidic in the colon caused by increase motility may advantageously facilitate the dissolution or absorption of the therapeutic agent.

20 Claims, 18 Drawing Sheets

(56) References Cited

U.S. PATENT DOCUMENTS

| | | | |
|---|---|---|---|
| 6,039,975 A | 3/2000 | Shah et al. | |
| 6,074,689 A | 6/2000 | Luck et al. | |
| 6,096,731 A | 8/2000 | McDonald | |
| 6,231,888 B1 | 5/2001 | Lerner et al. | |
| 6,309,663 B1* | 10/2001 | Patel .................. | A61P 7/02 424/463 |
| 6,326,364 B1 | 12/2001 | Lin et al. | |
| 6,444,477 B1 | 9/2002 | Borman et al. | |
| 6,747,014 B2 | 6/2004 | Teng et al. | |
| 6,949,258 B2 | 9/2005 | Zhang | |
| 7,070,803 B2 | 7/2006 | Skinhoj et al. | |
| 7,576,067 B2* | 8/2009 | Weinbach .................. | A61P 1/04 424/494 |
| 8,080,579 B2 | 12/2011 | Teitelbaum et al. | |
| 8,263,112 B2 | 9/2012 | Simon et al. | |
| 8,273,376 B2 | 9/2012 | Andremont et al. | |
| 8,277,843 B2 | 10/2012 | Singh et al. | |
| 8,318,663 B2 | 11/2012 | Young et al. | |
| 8,470,885 B2 | 6/2013 | Szewczyk | |
| 8,535,713 B2 | 9/2013 | Coulter | |
| 8,717,032 B2 | 5/2014 | Horman et al. | |
| 8,796,338 B2 | 8/2014 | Baron et al. | |
| 8,911,777 B2 | 12/2014 | Coulter | |
| 9,114,071 B2 | 8/2015 | Coulter | |
| 9,149,439 B2 | 10/2015 | Patel et al. | |
| 9,278,070 B2 | 3/2016 | Coulter et al. | |
| 9,301,938 B2 | 4/2016 | Szewczyk | |
| 9,463,170 B2 | 10/2016 | Baron et al. | |
| 9,907,755 B2 | 3/2018 | Kabadi et al. | |
| 10,154,972 B2 | 12/2018 | Baron et al. | |
| 10,182,993 B2 | 1/2019 | Yang et al. | |
| 10,188,646 B2 | 1/2019 | Gedulin et al. | |
| 10,441,604 B2 | 10/2019 | Gillberg et al. | |
| 10,441,605 B2 | 10/2019 | Gillberg et al. | |
| 10,722,457 B2 | 7/2020 | Gillberg et al. | |
| 10,786,529 B2 | 9/2020 | Gillberg et al. | |
| 10,840,112 B2 | 11/2020 | Sun et al. | |
| 10,864,170 B2 | 12/2020 | Fahmy et al. | |
| 10,881,685 B2 | 1/2021 | Gillberg et al. | |
| 11,007,142 B2 | 5/2021 | Gillberg et al. | |
| 2008/0182816 A1 | 7/2008 | Tam et al. | |
| 2009/0246301 A1 | 10/2009 | Ehrenpreis et al. | |
| 2010/0015224 A1 | 1/2010 | Singh et al. | |
| 2010/0130426 A1 | 5/2010 | Young et al. | |
| 2010/0209520 A1 | 8/2010 | Kubo | |
| 2010/0272797 A1 | 10/2010 | Kim et al. | |
| 2011/0268794 A1 | 11/2011 | Camilleri et al. | |
| 2015/0174076 A1 | 6/2015 | Harris et al. | |
| 2016/0228490 A1 | 8/2016 | Arnold et al. | |
| 2016/0235745 A1 | 8/2016 | Young et al. | |
| 2016/0303133 A1 | 10/2016 | Dudley et al. | |
| 2017/0266117 A1 | 9/2017 | Oliveira Varum et al. | |
| 2018/0193621 A1 | 7/2018 | Bonner et al. | |
| 2019/0046451 A1 | 2/2019 | Gillberg et al. | |
| 2020/0046757 A1 | 2/2020 | Gillberg et al. | |
| 2020/0046758 A1 | 2/2020 | Gillberg et al. | |
| 2020/0046759 A1 | 2/2020 | Taglienti et al. | |
| 2020/0163933 A1 | 5/2020 | Sampson et al. | |
| 2020/0330545 A1 | 10/2020 | Gillberg et al. | |
| 2021/0169901 A1 | 6/2021 | Halpern et al. | |

FOREIGN PATENT DOCUMENTS

| | | |
|---|---|---|
| EP | 3 646 857 A1 | 5/2020 |
| JP | S60-069028 A | 4/1985 |
| JP | 2003-160496 A | 6/2003 |
| JP | 2011-500558 A | 1/2011 |
| WO | WO 97/18816 A2 | 5/1997 |
| WO | WO 00/16784 A1 | 3/2000 |
| WO | WO 00/62810 A1 | 10/2000 |
| WO | WO 01/30322 A1 | 5/2001 |
| WO | WO 2007/019888 A2 | 2/2007 |
| WO | WO 2008/117814 A1 | 10/2008 |
| WO | WO 2009/038591 A1 | 3/2009 |
| WO | WO 2010/024576 A2 | 3/2010 |
| WO | WO 2010/080730 A2 | 7/2010 |
| WO | WO 2011/012989 A1 | 2/2011 |
| WO | WO 2011/075539 A2 | 6/2011 |
| WO | WO 2012/012902 A1 | 2/2012 |
| WO | WO 2012/097155 A1 | 7/2012 |
| WO | WO 2012/148991 A1 | 11/2012 |
| WO | WO 2012/151252 A2 | 11/2012 |
| WO | WO 2013/103919 A2 | 7/2013 |
| WO | WO 2014/011926 A1 | 1/2014 |
| WO | WO 2014/066053 A2 | 5/2014 |
| WO | WO 2017/172816 A1 | 10/2017 |
| WO | WO 2020/014334 A1 | 1/2020 |

OTHER PUBLICATIONS

International Preliminary Report on Patentability for International Application No. PCT/US20/45987, mailed Feb. 24, 2022.

Abrahamsson et al., Altered bile acid metabolism in patients with constipation-predominant irritable bowel syndrome and functional constipation. Scand J Gastroenterol. 2008;43(12):1483-8. doi: 10.1080/00365520802321212.

Amidon et al., Colon-targeted oral drug delivery systems: design trends and approaches. AAPS PharmSciTech. Aug. 2015;16(4):731-41. doi: 10.1208/s12249-015-0350-9. Epub Jun. 13, 2015.

Appleby et al., The role of bile acids in functional GI disorders. Neurogastroenterol Motil. Aug. 2014;26(8):1057-69. doi: 10.1111/nmo.12370. Epub Jun. 5, 2014.

Bampton et al., The proximal colonic motor response to rectal mechanical and chemical stimulation. Am J Physiol Gastrointest Liver Physiol. Mar. 2002;282(3):G443-9. doi: 10.1152/ajpgi.00194.2001.

Camilleri et al., Therapeutic targeting of bile acids. Am J Physiol Gastrointest Liver Physiol. Aug. 15, 2015;309(4):G209-15. doi: 10.1152/ajpgi.00121.2015. Epub Jul. 2, 2015.

Camilleri, Bile Acid diarrhea: prevalence, pathogenesis, and therapy. Gut Liver. May 23, 2015;9(3):332-9. doi: 10.5009/gnl14397.

Casellas et al., Bile acid induced colonic irritation stimulates intracolonic nitric oxide release in humans. Gut. May 1996;38(5):719-23. doi: 10.1136/gut.38.5.719.

Cummings et al., The control and consequences of bacterial fermentation in the human colon. J Appl Bacteriol. Jun. 1991;70(6):443-59. doi: 10.1111/j.1365-2672.1991.tb02739.x.

Davis et al., Transit of pharmaceutical dosage forms through the small intestine. Gut. Aug. 1986;27(8):886-92. doi: 10.1136/gut.27.8.886.

Del Curto et al., Erodible Time-Dependent Colon Delivery Systems with Improved Efficiency in Delaying the Onset of Drug Release. Journal of Pharmaceutical Sciences. Nov. 2014;103(11):3585-93. Epub Jan. 4, 2016.

Duboc et al., Increase in fecal primary bile acids and dysbiosis in patients with diarrhea-predominant irritable bowel syndrome. Neurogastroenterol Motil. Jun. 2012;24(6):513-20, e246-7. doi: 10.1111/j.1365-2982.2012.01893.x. Epub Feb. 22, 2012.

Edwards et al., Effect of bile acid on anorectal function in man. Gut. Mar. 1989;30(3):383-6. doi: 10.1136/gut.30.3.383.

Fukata et al., The effective therapy of cyclosporine A with drug delivery system in experimental colitis. Journal of Drug Targeting. 2011;19(6):458-67. Epub Aug. 30, 2010.

Hegyi et al., Guts and Gall: Bile Acids in Regulation of Intestinal Epithelial Function in Health and Disease. Physiol Rev. Oct. 1, 2018;98(4):1983-2023. doi: 10.1152/physrev.00054.2017.

Hickson, Probiotics in the prevention of antibiotic-associated diarrhoea and Clostridium difficile infection. Therap. Adv. Gastroenterol. May 2011;4(3):185-97.

Ibekwe et al., A new concept in colonic drug targeting: a combined pH-responsive and bacterially-triggered drug delivery technology. Aliment Pharmacol Ther. Oct. 1, 2008;28(7):911-6.

Ibekwe et al., An investigation into the in vivo performance variability of pH responsive polymers for ileo-colonic drug delivery using gamma scintigraphy in humans. J Pharm Sci. Dec. 2006;95(12):2760-6. doi: 10.1002/jps.20742.

(56) References Cited

OTHER PUBLICATIONS

Igimi et al., pH-Solubility relations of chenodeoxycholic and ursodeoxycholic acids: physical-chemical basis for dissimilar solution and membrane phenomena. Journal of Lipid Research. 1980;21:72-90.
Jia et al., Bile acid-microbiota crosstalk in gastrointestinal inflammation and carcinogenesis. Nat Rev Gastroenterol Hepatol. Feb. 2018;15(2):111-128. doi: 10.1038/nrgastro.2017.119. Epub Oct. 11, 2017. Author manuscript provided. 41 pages.
Kirwan et al., Bile acids and colonic motility in the rabbit and the human. Gut. 1975;16:894-902.
Lee et al., Targeted Approaches for In Situ Gut Microbiome Manipulation. Genes. 2018;9:351. Epub Jul. 12, 2018. 12 pages.
Mekhjian et al., Colonic absorption of unconjugated bile acids: perfusion studies in man. Dig Dis Sci. Jul. 1979;24(7):545-50. doi: 10.1007/BF01489324.
Mekhjian et al., Colonic Secretion of Water and Electrolytes Induced by Bile Acids: Perfusion Studies in Man. The Journal of Clinical Investigation. 1971;50(8):1569-77.
Mok et al., Effect of different doses of chenodeoxycholic acid on bile-lipid composition and on frequency of side-effects in patients with gallstones. Lancet. Aug. 3, 1974;2(7875):253-7. doi: 10.1016/s0140-6736(74)91415-9.
Mudie et al., Quantification of gastrointestinal liquid volumes and distribution following a 240 mL dose of water in the fasted state. Mol Pharm. Sep. 2, 2014;11(9):3039-47. doi: 10.1021/mp500210c. Epub Aug. 19, 2014.
Muheem et al., A review on the strategies for oral delivery of proteins and peptides and their clinical perspectives. Saudi Pharm J. Jul. 2016;24(4):413-28. doi: 10.1016/j.jsps.2014.06.004. Epub Jun. 16, 2014.
Murray et al., Magnetic Resonance Imaging Quantification of Fasted State Colonic Liquid Pockets in Healthy Humans. Mol Pharm. Aug. 7, 2017;14(8):2629-2638. doi: 10.1021/acs.molpharmaceut.7b00095. Epub Jul. 6, 2017.
Nardelli et al., MMX® technology and its applications in gastrointestinal diseases. Therap. Adv. Gastroenterol. Jul. 2017;10(7):545-52. Epub May 25, 2017.
Placidi et al., PTH-045 Effects of an osmotic laxative on the distribution of water between the small and large intestine in humans. Gut. 2015;59(Suppl 1):A141. Epub Sep. 23, 2015.
Pritchard et al., Fasting and postprandial volumes of the undisturbed colon: normal values and changes in diarrhea-predominant irritable bowel syndrome measured using serial MRI. Neurogastroenterol Motil. Jan. 2014;26(1):124-30. doi: 10.1111/nmo.12243. Epub Oct. 17, 2013.
Rao et al., Chenodeoxycholate in females with irritable bowel syndrome-constipation: a pharmacodynamic and pharmacogenetic analysis. Gastroenterology. Nov. 2010;139(5):1549-58, 1558.e1. doi: 10.1053/j.gastro.2010.07.052. Epub Aug. 4, 2010. Author manuscript provided. 19 pages.
Rao et al., Evaluation of gastrointestinal transit in clinical practice: position paper of the American and European Neurogastroenterology and Motility Societies. Neurogastroenterol Motil. Jan. 2011;23(1):8-23. doi: 10.1111/j.1365-2982.2010.01612.x.
Schiller et al., Intestinal fluid volumes and transit of dosage forms as assessed by magnetic resonance imaging. Aliment Pharmacol Ther. Nov. 15, 2005;22(10):971-9. doi: 10.1111/j.1365-2036.2005.02683.x.
Shin et al., Bowel functions, fecal unconjugated primary and secondary bile acids, and colonic transit in patients with irritable bowel syndrome. Clin Gastroenterol Hepatol. Oct. 2013;11(10):1270-1275.e1. doi: 10.1016/j.cgh.2013.04.020. Epub Apr. 30, 2013. Author manuscript provided. 13 pages.
Steiger et al., Controlled Delivery of Bile Acids to the Colon. Clinical and Translational Gastroenterology. Dec. 2020;11(12):e00229. Epub Dec. 1, 2020. 8 pages.
Tomita et al., Study of segmental colonic transit time in healthy men. Hepatogastroenterology. Sep.-Oct. 2011;58(110-111):1519-22. doi: 10.5754/hge10849. Epub Jul. 15, 2011.
Vijayvargiya et al., Bile Acid Deficiency in a Subgroup of Patients With Irritable Bowel Syndrome With Constipation Based on Biomarkers in Serum and Fecal Samples. Clin Gastroenterol Hepatol. Apr. 2018;16(4):522-527. doi: 10.1016/j.cgh.2017.06.039. Epub Jun. 27, 2017. Author manuscript provided. 17 pages.
Extended European Search Report for EP Application No. 20852057.7 dated Jun. 9, 2023.
Odunsi-Shiyanbade et al., Effects of chenodeoxycholate and a bile acid sequestrant, colesevelam, on intestinal transit and bowel function. Clin Gastroenterol Hepatol. Feb. 2010;8(2):159-65. doi: 10.1016/j.cgh.2009.10.020. Epub Oct. 30, 2009.
Singaporean Search Report and Written Opinion mailed Nov. 13, 2023, for Application No. 11202200380R.

\* cited by examiner

ARTICLES AND METHODS FOR ADMINISTRATION OF THERAPEUTIC AGENTS

RELATED APPLICATIONS

This application is a continuation of U.S. application Ser. No. 16/991,536, filed Aug. 12, 2020, and entitled "ARTICLES AND METHODS FOR ADMINISTRATION OF THERAPEUTIC AGENTS," which claims priority under 35 U.S.C. § 119 (e) to U.S. Provisional Application No. 62/885,450, filed Aug. 12, 2019, and entitled "ARTICLES AND METHODS FOR ADMINISTRATION OF THERAPEUTIC AGENTS," each of which is incorporated herein by reference in its entirety for all purposes.

TECHNICAL FIELD

Articles and methods related to administration of a therapeutic agent to the colon of a subject are generally described.

BACKGROUND

Local and controlled delivery of drugs to the colon persists as a challenge in the delivery of pharmaceuticals to the gastrointestinal tract. Novel technologies that can address this issue stand to improve the efficacy of drugs while reducing the likelihood of adverse effects. Accordingly, improved methods of drug delivery to the colon are needed.

SUMMARY

The subject matter of the present invention involves, in some cases, interrelated products, alternative solutions to a particular problem, and/or a plurality of different uses of one or more systems and/or articles.

In one aspect, articles configured for release of a therapeutic agent in a colon of a subject are provided. In some embodiments, the article comprises a first portion comprising a secretion inducing agent, a second portion adjacent the first portion, the second portion comprising a therapeutic agent, and a degradable coating associated with the article.

In some embodiments, the article comprises a first component configured to increase the amount of intestinal fluid present in the intestine of the subject and a second component associated with the first component configured to release a therapeutic agent in the intestine of the subject.

In another aspect, methods are provided. In some embodiments, the method comprises exposing a portion of an intestine of a subject to an intestinal secretion inducing agent such that the intestine is induced to release intestinal fluids and providing a therapeutic agent to a portion of a intestine of the subject, wherein the secretion inducing agent increases the amount of the therapeutic agent available for absorption by the intestine of the subject.

In some embodiments, the method comprises administering, to a subject, an article, the article comprising a first portion comprising a secretion inducing agent, a second portion adjacent the first portion, the second portion comprising the therapeutic agent, and a degradable coating associated with the article, wherein the secretion inducing agent is configured to increase an amount of intestinal fluid present in an intestine of the subject and releasing the therapeutic agent from article to the intestine of the subject.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
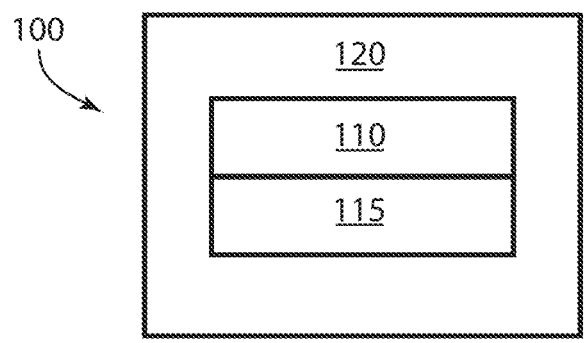
FIG. 1 shows a schematic diagram of an exemplary article configured for the controlled release of a therapeutic agent, according to one set of embodiments.

Articles and methods for delivering a therapeutic agent to a subject are described. These articles and methods may be useful, in some cases, for the delivery of therapeutic agents to the colon of a subject. In some embodiments, an article is configured to release a secretion inducing agent e.g., to stimulate the release of intestinal fluids. The article, in some embodiments, comprises a therapeutic agent such that the stimulated release of intestinal fluid increases the amount of therapeutic agent available for absorption by the colon. For example, in some embodiments, the articles and methods described herein advantageously promote increased absorption of therapeutic agents in subjects as compared to traditionally administered therapeutic agents without additional components such as a secretion inducing agent. In some embodiments, articles and methods described herein may increase the motility of the colon of a subject. The increase in contractions and movement of fluidic in the colon caused by increase motility may advantageously facilitate the dissolution or absorption of the therapeutic agent.

In one aspect, an article is described that is configured to release a therapeutic agent to the colon of a subject. The article may have a first portion comprising a secretion inducing agent, a second portion comprising a therapeutic agent, and a degradable coating associated with the article. In some embodiments, the article is absent a coating. In some embodiments, the article is a pill, a tablet, or a capsule, which may be administered orally to a subject.

In another aspect, an article is described that is configured for release of a therapeutic agent in a portion of an intestine of a subject. The article may comprise a first component configured to increase the amount of intestinal fluid present in the intestine of a subject and a second component associated with the first component configured to release a therapeutic agent in the intestine of the subject.

In yet another aspect, a method is described for intestinal drug delivery. The method comprises exposing a portion of an intestine to an intestinal secretion inducing agent such that the intestine is induced to release intestinal fluid. The method may also comprise providing a therapeutic agent to a portion of the intestine wherein the secretion inducing agent increases the amount of therapeutic agent available for absorption by the intestine of the subject.

In yet another aspect still, a method of administering a therapeutic agent is described. The method may comprise administering an article to a subject where the article may comprise a secretion inducing agent, a second portion adjacent to the first portion, the second portion comprising the therapeutic agent, and a degradable coating associated with the article. The secretion inducing agent may be configured to increase an amount of intestinal fluid present in the intestine and the method may involve releasing a therapeutic agent from the article to the intestine of the subject.

Certain embodiments of the article have an associated degradable coating. In some embodiments, and without wishing to be bound by theory, the degradable coating enables tuning of a release location along the intestinal tract of the subject where the secretion inducing agent and the therapeutic agent is released. In some embodiments, the stimulated release of the intestinal fluids by the secretion inducing agent enhances the local solubility of the therapeutic agent along the colon.

A "subject", as used herein, refers to any animal such as a mammal (e.g., a human). Non-limiting examples of subjects include a human, a non-human primate, a cow, a horse, a pig, a sheep, a goat, a dog, a cat or a rodent such as a mouse, a rat, a hamster, a bird, a fish, or a guinea pig. The embodiments described herein may be, in some cases, directed toward use with humans. In some embodiments, a subject may demonstrate health benefits, e.g., upon administration of the articles described herein.

Certain embodiments of the invention advantageously provide for the enhanced solubility of a therapeutic agent in the colon. In embodiments where the article is configured with a coating, the coating mat be advantageously be configured such that the secretion inducing agent is released in desired locations of the colon (e.g., as opposed to other undesired and/or less effective portions of the digestive tract). In certain cases, the coating is configured to prevent (e.g., substantially inhibit) the release of the secretion inducing agent in a location along the gastrointestinal (GI) tract in a manner that may cause abdominal pain to the subject (for example, the coating may prevent the burst release of a secretion inducing agent).

In one set of embodiments, the secretion inducing agent is a bile acid, such a chenodeoxycholic acid (CDC). In some embodiments, when configured with a suitable coating, for example, an enteric polymer sold under the trademark EUDRAGIT® S100, articles described herein advantageously do not substantially release the secretion inducing agent or the therapeutic agent until reaching a desired location for release (e.g., distal part of the ileum). In some embodiments, upon reaching the desired location, the degradable coating releases the secretion inducing agent to produce a local internal concentration of the secretion inducing agent e.g., of at least 3 mM or at least 5 mM at a location internal to the subject. Without wishing to be bound by theory, a local increase in the concentration of secretion inducing agents may, in some cases, stimulate the release of (additional) intestinal fluids, thereby enhancing the solubility of a desired therapeutic agent (e.g., the therapeutic agent of the article described herein). In certain embodiments, the secretion inducing agent may also increase the motility of the colon to advantageously enhance the dissolution and/or absorption of the therapeutic agent. In some embodiments, this therapeutic agent may be a bile acid or a salt thereof, such as sodium chenodeoxycholate (NaCDC).

In some embodiments, the article comprises a first portion, comprising a secretion inducing agent, adjacent a second portion, comprising a therapeutic agent. As used herein, when a portion or layer is referred to as being "adjacent." it may be directly adjacent to another component or portion, or one or more intervening components (e.g., portions including, but not limited to portions comprising a therapeutic agent and portions comprising a secretion inducing agent) also may be present. A portion or layer that is "directly adjacent" to another portion/layer means that no intervening component is present.

FIG. 1 shows a non-limiting example of an article configured for delivery of a therapeutic agent. In some embodiments, article 100 has a first portion 110 (e.g., comprising a secretion inducing agent) and a second portion 115 (e.g., comprising a therapeutic agent) adjacent to first portion 110. In some embodiments, a coating 120 may be associated with article 100. In some embodiments, coating 120 may be configured to protect (e.g., from dissolution) first portion 110 and/or second portion 115 until reaching a desired location internal to the subject. In some embodiments, first portion 110 is a first layer and second portion 120 is a second layer in article 100. While first portion 110 and second portion 120 are depicted in FIG. 1, one or more additional portions and/or layers may also be present in article 100.

While FIG. 1 is shown as coating 120 surrounding article 100, in some embodiments, coating 120 may only partially surround article 100, or coating 120 may be absent. In some embodiments, first portion 110 and second portion 115 may be in direct contact as depicted in FIG. 1. In some embodiments, first portion 110 and second portion 115 may be spatially separated (e.g., one or more layers and/or components may be positioned between first portion 110 and second portion 115). In certain embodiments, first portion 110 and the second portion 115 may be encapsulated in distinct or overlapping portions of coating 120.

Figure 2:
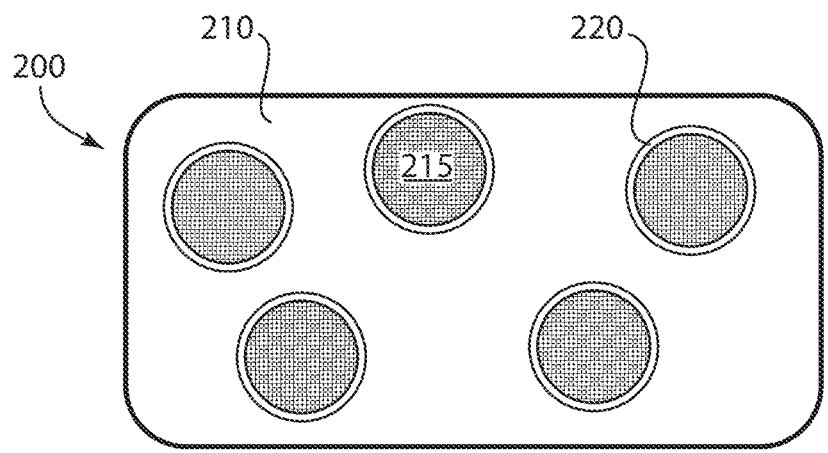
FIG. 2 shows a schematic diagram of an exemplary article configured for the controlled release of a therapeutic agent, according to one set of embodiments.

In another embodiment, referring now to FIG. 2., a non-limiting schematic example of an article configured for delivery of a therapeutic agent is shown. Article 200 comprises a first portion 210 (e.g., comprising a secretion inducing agent) and a second portion 215 (e.g., comprising a therapeutic agent) adjacent first portion 210. In some embodiments, a coating 220 may be associated with second portion 215, as depicted in FIG. 2. In some embodiments, a coating may be associated with first portion 210 (e.g., at least partially encapsulating first portion 210, fully encapsulating first portion 210). In some embodiments, coating 220 may be configured to protect (e.g., from dissolution) second portion 215 but dissolve before first portion 210. In some embodiments, first portion 210 may surround second portion 215 and coating 215 prior to administration to a subject. While first portion 210 and second portion 220 are depicted in FIG. 2, one or more additional portions and/or coatings may also be present in article 200.

While FIG. 2 is shown as coating 220 surrounding second portion 215, some embodiments of articles described may have coating 220 only partially surrounding second portion 215 or coating 220 may be absent. In some embodiments, first portion 210 and second portion 215 may be in direct contact without a coating. In some embodiments, first portion 210 and second portion 215 may be spatially separated (e.g., one or more portions and/or components may be positioned between first portion 210 and second portion 215).

In some embodiments, a ratio of the first portion (e.g., comprising a secretion-inducing agent) and the second portion (e.g., comprising a therapeutic agent) is greater than or equal to 1:1, greater than or equal to 1:2, greater than or equal to 1:3, greater than or equal to 1:4, greater than or equal to 1:5; greater than or equal to 1:10, greater than or equal to 1:20, greater than or equal to 1:30, greater than or equal to 1:40, greater than or equal to 1:50, greater than or equal to 1:60, greater than or equal to 1:70, greater than or equal to 1:75, greater than or equal to 1:80, greater than or equal to 1:85, greater than or equal to 1:90, greater than or equal to 1:95, greater than or equal to 1:96, greater than or equal to 1:97, greater than or equal to 1:98, or greater than or equal to 1:99. In some embodiments, a ratio of the first portion to the second portion is less than or equal to 1:99, less than or equal to 1:98, less than or equal to 1:97, less than or equal to 1:96, less than or equal to 1:95, less than or equal to 1:90, less than or equal to 1:85, less than or equal to 1:80, less than or equal to 1:75, less than or equal to 1:70, less than or equal to 1:60, less than or equal to 1:50, less than or equal to 1:40, less than or equal to 1:30, less than or equal to 1:20, less than or equal to 1:10, less than or equal to 1:5, less than or equal to 1:4, less than or equal to 1:3, less than or equal to 1:2, or less than or equal to 1:1. Combinations of the above-referenced ranges are also possible (e.g., greater than or equal to 1:1 and less than or equal to 1:99). Other ranges are possible. Selecting a particular ratio of the first portion (e.g., comprising the secretion-inducing agent) and the second portion (e.g., comprising the therapeutic agent) can advantageously control the release of the therapeutic agent. Those skilled in the art based on the teachings of the present disclosure will be capable of selection an appropriate ratio of the first portion and the second portion.

In some embodiments, a ratio of the second portion (e.g., comprising a therapeutic agent) and the first portion (e.g., comprising a secretion-inducing agent) is greater than or equal to 1:1, greater than or equal to 1:2, greater than or equal to 1:3, greater than or equal to 1:4, greater than or equal to 1:5; greater than or equal to 1:10, greater than or equal to 1:20, greater than or equal to 1:30, greater than or equal to 1:40, greater than or equal to 1:50, greater than or equal to 1:60, greater than or equal to 1:70, greater than or equal to 1:75, greater than or equal to 1:80, greater than or equal to 1:85, greater than or equal to 1:90, greater than or equal to 1:95, greater than or equal to 1:96, greater than or equal to 1:97, greater than or equal to 1:98, or greater than or equal to 1:99. In some embodiments, a ratio of the second portion to the first portion is less than or equal to 1:99, less than or equal to 1:198, less than or equal to 1:97, less than or equal to 1:96, less than or equal to 1:95, less than or equal to 1:90, less than or equal to 1:85, less than or equal to 1:80, less than or equal to 1:75, less than or equal to 1:70, less than or equal to 1:60, less than or equal to 1:50, less than or equal to 1:40, less than or equal to 1:30, less than or equal to 1:20, less than or equal to 1:10, less than or equal to 1:5, less than or equal to 1:4, less than or equal to 1:3, less than or equal to 1:2, or less than or equal to 1:1. Combinations of the above-referenced ranges are also possible (e.g., greater than or equal to 1:1 and less than or equal to 1:99). Other ranges are possible.

Figure 3:
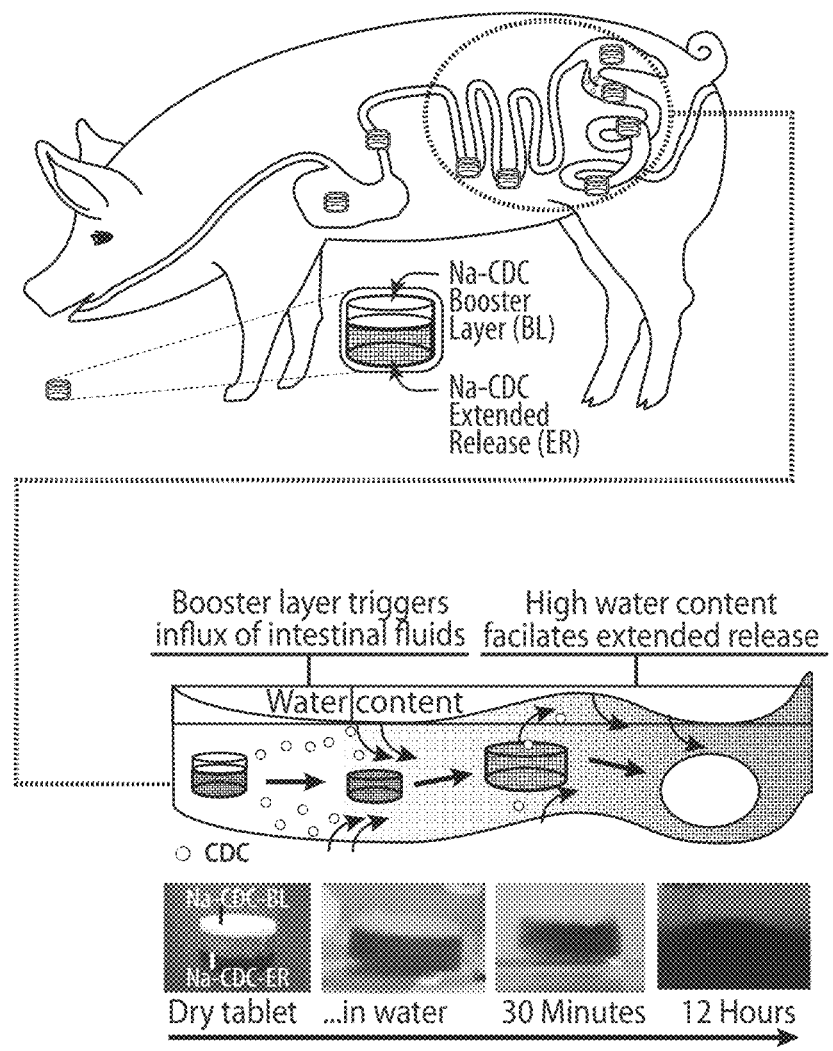
FIG. 3 shows a schematic illustration of an exemplary article moving through the gastrointestinal tract of a subject, according to one set of embodiments.

In some embodiments, an article (e.g. a tablet comprising a secretion inducing agent and a therapeutic agent) may be administered to a subject orally where, in some cases, it travels through the gastrointestinal tract of the subject until reaching a desired internal location. For example, as illustrated schematically in FIG. 3, an article configured for release of a therapeutic agent may be administered to a subject (e.g., orally) such it enters the gastrointestinal tract of the subject. In some embodiments, upon reaching the colon of the subject, the coating at least partially degrade to expose a first portion comprising a secretion inducting agent. The secretion inducing agent stimulates the release of additional intestinal fluids. The second portion comprising a therapeutic agent, in some embodiments, dissolves such that the therapeutic agent is released at a location internal to the subject. In some embodiments, advantageously, the release of additional intestinal fluids may also help to improve the dissolution and/or solubility of the therapeutic agent and/or enhance the amount absorbed by the colon.

In some embodiments, a secretion inducing agent may be provided. As used herein, a secretion inducing agent generally refers to a chemical species that stimulates the release of increased intestinal fluid along the gastrointestinal tract (e.g., relative to the basal release of intestinal fluid and/or the basal release of intestinal fluid in response to a foreign body present in the gastrointestinal tract such as food). In this way, the increased amount of intestinal fluid present enhances the solubility and/or the absorption of a therapeutic agent. In some embodiments, the secretion inducing agent is a bile acid or a salt thereof. In some embodiments, the bile acid is chendeoxycholic acid. In certain embodiments, this secretion inducing agent is a salt of chendeoxycholic acid, e.g., sodium chendeoxycholate (NaCDC). In some embodiments, the secretion inducing agent comprises bisacodyl, *senna*, sennoside, linaclotide, plecanatide, lubiprostone, methylnaltrexone, naloxegol, polyethylene glycole, lactulose, or prucalopride. In some embodiments, the secretion inducing agent may be a salt, such as magnesium citrate, magnesium hydroxide, or a bile salt, as non-limiting examples. Other secretion inducing agents are possible, as any chemical species that stimulates the release of intestinal fluid along the gastrointestinal tract may be function as a secretion inducing agent.

In some embodiments, the wt % of the secretion-inducing agent relative to the total weight of the article (e.g., a tablet, a capsule) is greater than or equal to 10 wt %, greater than or equal to 15 wt %, greater than or equal to 20 wt %, greater than or equal to 25 wt %, greater than or equal to 30 wt %, greater than or equal 40 wt %, greater than or equal to 50 wt %, greater than or equal to 60 wt %, greater than or equal to 70 wt %, greater than or equal to 75 wt %, greater than or equal to 80 wt %, greater than or equal 90 wt %, or greater than or equal to 95 wt %. In some embodiments, the wt % of the secretion-inducing agent relative to the total weight of the article is less than or equal to 95 wt %, less than or equal to 90 wt %, less than or equal to 80 wt %, less than or equal to 75 wt %, less than or equal to 70 wt %, less than or equal to 60 wt %, less than or equal to 50 wt %, less than or equal to 40 wt %, less than or equal to 30 wt %, less than or equal to 25 wt %, less than or equal to 20 wt %, less than or equal to 15 wt %, or less than or equal to 10 wt %. Combinations of the above-references ranges are also possible (e.g., greater than or equal to 10 wt % and less than or equal to 50 wt %). Other ranges are possible.

In some embodiments, the amount (e.g., the mass) of the secretion-inducing agent present in the article (e.g., in a capsule, in a tablet) is greater than or equal to 5 mg, greater than or equal to 10 mg, greater than or equal to 20 mg, greater than or equal to 25 mg, greater than or equal to 30 mg, greater than or equal to 50 mg, greater than or equal to 60 mg, greater than or equal to 70 mg, greater than or equal to 75 mg, greater than or equal to 80 mg, greater than or equal to 90 mg, greater than or equal to 95 mg, greater than or equal to 100 mg, greater than or equal to 250 mg, greater than or equal to 500 mg, greater than or equal to 750 mg, greater than or equal to 1 g, greater than or equal to 2 g, greater than or equal to 3 g, greater than or equal to 4 g, or greater than or equal to 5 g. In some embodiments, the amount of the secretion-inducing agent is less than or equal to 5 g, less than or equal to 4 g, less than or equal to 3 g, less than or equal to 2 g, less than or equal to 1 g, less than or equal to 750 mg, less than or equal to 500 mg, less than or equal to 250 mg, less than or equal to 100 mg, less than or equal to 95 mg, less than or equal to 90 mg, less than or equal 80 mg, less than or equal to 75 mg, less than or equal to 70 mg, less than or equal to 60 mg, less than or equal to 50 mg, less than or equal to 40 mg, less than or equal to 30 mg, less than or equal to 25 mg, less than or equal to 20 mg, less than or equal to 10 mg, or less than or equal to 5 mg. Combinations of the above-referenced ranges are also possible (e.g., greater than or equal to 5 mg and less than or equal to 5 g). Other ranges are possible.

Certain embodiments comprise a therapeutic agent associated with the article, as described herein. According to some embodiments, the therapeutic agent may be one or a combination of therapeutic, diagnostic, and/or enhancement agents, such as drugs, nutrients, microorganisms, in vivo sensors, and tracers. In some embodiments, the therapeutic agent is a nutraceutical, prophylactic or diagnostic agent. While much of the specification describes the use of therapeutic agents, other agents listed herein are also possible. Agents can include, but are not limited to, any synthetic or naturally-occurring biologically active compound or composition of matter which, when administered to a subject (e.g., a human or nonhuman animal), induces a desired pharmacologic, immunogenic, and/or physiologic effect by local and/or systemic action, such as increasing the amount of intestinal fluid present in the colon of a subject. For example, useful or potentially useful within the context of certain embodiments are compounds or chemicals traditionally regarded as drugs, vaccines, and biopharmaceuticals. Certain such agents may include molecules such as proteins, peptides, hormones, nucleic acids, gene constructs, etc., for use in therapeutic, diagnostic, and/or enhancement areas, including, but not limited to medical or veterinary treatment, prevention, diagnosis, and/or mitigation of disease or illness (e.g., HMG-COA reductase inhibitors (statins) like rosuvastatin, nonsteroidal anti-inflammatory drugs like meloxicam, selective serotonin reuptake inhibitors like escitalopram, blood thinning agents like clopidogrel, steroids like prednisone, antipsychotics like aripiprazole and risperidone, analgesics like buprenorphine, antagonists like naloxone, montelukast, and memantine, cardiac glycosides like digoxin, alpha blockers like tamsulosin, cholesterol absorption inhibitors like ezetimibe, metabolites like colchicine, antihistamines like loratadine and cetirizine, opioids like loperamide, proton-pump inhibitors like omeprazole, anti (retro) viral agents like entecavir, dolutegravir, rilpivirine, and cabotegravir, antibiotics like doxycycline, ciprofloxacin, and azithromycin, anti-malarial agents, and synthroid/levothyroxine); substance abuse treatment (e.g., methadone and varenicline); family planning (e.g., hormonal contraception); performance enhancement (e.g., stimulants like caffeine); and nutrition and supplements (e.g., protein, folic acid, calcium, iodine, iron, zinc, thiamine, niacin, vitamin C, vitamin D, and other vitamin or mineral supplements).

In certain embodiments, the therapeutic agent is one or more specific therapeutic agents. As used herein, the term "therapeutic agent" (or also referred to as a "drug") refers to an agent that is administered to a subject to treat a disease, disorder, or other clinically recognized condition, or for prophylactic purposes, and has a clinically significant effect on the body of the subject to treat and/or prevent the disease, disorder, or condition. Listings of examples of known therapeutic agents can be found, for example, in the United States Pharmacopeia (USP), Goodman and Gilman's The Pharmacological Basis of Therapeutics, 10th Ed., McGraw Hill, 2001; Katzung, B. (ed.) Basic and Clinical Pharmacology, McGraw-Hill/Appleton & Lange; 8th edition (Sep. 21, 2000); Physician's Desk Reference (Thomson Publishing), and/or The Merck Manual of Diagnosis and Therapy, 17th ed. (1999), or the 18th ed (2006) following its publication, Mark H. Beers and Robert Berkow (eds.), Merck Publishing Group, or, in the case of animals, The Merck Veterinary Manual, 9th ed., Kahn, C. A. (ed.), Merck Publishing Group, 2005; and "Approved Drug Products with Therapeutic Equivalence and Evaluations," published by the United States Food and Drug Administration (F.D.A.) (the "Orange Book"). Examples of drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. In certain embodiments, the therapeutic agent is a small molecule. Exemplary classes of therapeutic agents include, but are not limited to, analgesics, anti-analgesics, anti-inflammatory drugs, antipyretics, antidepressants, antiepileptics, antipsychotic agents, neuroprotective agents, anti-proliferatives, such as anti-cancer agents, antihistamines, antimigraine drugs, hormones, prostaglandins, antimicrobials (including antibiotics, antifungals, antivirals, antiparasitics), antimuscarinics, anxioltyics, bacteriostatics, immunosuppressant agents, sedatives, hypnotics, antipsychotics, bronchodilators, anti-asthma drugs, cardiovascular drugs, anesthetics, anti-coagulants, inhibitors of an enzyme, steroidal agents, steroidal or non-steroidal anti-inflammatory agents, corticosteroids, dopaminergics, electrolytes, gastro-intestinal drugs, muscle relaxants, nutritional agents, vitamins, parasympathomimetics, stimulants, anorectics and anti-narcoleptics. Nutraceuticals can also be incorporated into the drug delivery device. These may be vitamins, supplements such as calcium or biotin, or natural ingredients such as plant extracts or phytohormones.

In another embodiment, the therapeutic agent is an immunosuppressive agent. Exemplary immunosuppressive agents include glucocorticoids, cytostatics (such as alkylating agents, antimetabolites, and cytotoxic antibodies), antibodies (such as those directed against T-cell recepotors or Il-2 receptors), drugs acting on immunophilins (such as cyclosporine, tacrolimus, and sirolimus) and other drugs (such as interferons, opioids, TNF binding proteins, mycophenolate, and other small molecules such as fingolimod).

In certain embodiments, the therapeutic agent is a hormone or derivative thereof. Non-limiting examples of hormones include insulin, growth hormone (e.g., human growth hormone), vasopressin, melatonin, thyroxine, thyrotropin-releasing hormone, glycoprotein hormones (e.g., luteinzing hormone, follicle-stimulating hormone, thyroid-stimulating hormone), cicosanoids, estrogen, progestin, testosterone, estradiol, cortisol, adrenaline, and other steroids.

In some embodiments, the therapeutic agent is a bile acid. Bile acids are understood by those skilled in the art as steroid acids predominately in the bile of mammals (e.g. humans) and other vertebrates. For certain embodiments, the bile acid is in the form of a bile salt, i.e., the conjugate base of the bile acid and an appropriate cation (e.g. sodium, potassium, etc.). In certain embodiments, the bile salt is sodium chenodeoxycholic acid. Non-limiting examples of the bile acids (or salts thereof) include chenodeoxycholic acid, deoxycholic acid, taurocholic, glycocholic acid, choic acid, taurochenodeoxycholic acid, glycochenodeoxycholic acid, deoxycholic acid, and lithocholic acid. Other bile acids (and salts thereof) are possible as the disclosure is not so limited. While some bile acids have been used to attempt to treat conditions, such as irritable bowel syndrome with constipation, these attempts were associated with a high frequency of abdominal pain. However, the Inventors have recognized and appreciated that a controlled release using a bi-layered delivery system consisting of an immediate release layer and a controlled release layer could improve the frequency of abdominal pain, exemplified with a reduction in abdominal contractions of the subject. Without wishing to be bound by any theory, after disintegration of the bile acid, the local 'super-physiological' concentrations can trigger adverse effects in the proximal colon. Super-physiological bile acid concentrations have previously been linked to giant contractions and inflammation in the GI tract. While conventional colonic drug delivery systems, like the single layered release system, used as a control in some examples, can impair drug dissolution and solubility. However, it has been recognized and appreciated within the context of this disclosure that bilayered delivery system that first achieve a prosecretory local concentration of CDC (e.g., ~ 5 mM) can facilitate controlled release along the colon from a second layer.

In some embodiments, the therapeutic agent is a small molecule drug having molecular weight less than about 2500 Daltons, less than about 2000 Daltons, less than about 1500 Daltons, less than about 1000 Daltons, less than about 750 Daltons, less than about 500 Daltons, less or than about 400 Daltons. In some cases, the therapeutic agent is a small molecule drug having molecular weight between 200 Daltons and 400 Daltons, between 400 Daltons and 1000 Daltons, or between 500 Daltons and 2500 Daltons.

In some embodiments, the therapeutic agent is selected from the group consisting of active pharmaceutical agents such as bile acids, probiotics, polysaccharides (e.g. Reglemers™), compounds derived from fecal matter, glycans, antigen mimics, Cas nucleases, nucleic acids, peptides, proteins, bacteriophage, modified bacteria, DNA, mRNA, human growth hormone, monoclonal antibodies, adalimumab, epinephrine, GLP-1 Receptor agoinists, semaglutide, liraglutide, dulaglitide, exenatide, factor VIII, small molecule drugs, progrstin, vaccines, subunit vaccines, recombinant vaccines, polysaccharide vaccines, and conjugate vaccines, toxoid vaccines, influenza vaccine, shingles vaccine, prevnar pneumonia vaccine, MMR vaccine, tetanus vaccine, hepatitis vaccine, HIV vaccine Ad4 env Clade C, HIV vaccine Ad4-mGag, DNA vaccines, RNA vaccines, etanercept, infliximab, filgastrim, glatiramer acetate, rituximab, bevacizumab, any molecule encapsulated in a nanoparticle, epinephrine, lysozyme, glucose-6-phosphate dehydrogenase, other enzymes, certolizumab pegol, ustekinumab, ixckizumab, golimumab, brodalumab, guselkumab, secikinumab, omalizumab, TNF-alpha inhibitors, interleukin inhibitors, vedolizumab, octreotide, teriperatide, CRISPR-Cas9, antisense oligonucleotides, and ondansetron. In certain embodiments, the therapeutic agent may comprise a polyunsaturated fatty acid (e.g. butyric acid, propionic acid), an omega-3 fatty acid (e.g., docosahexaenoic acid, cicosapentaenoic acid), a bismuth salt e.g. (bismuth subgallate), or a polysaccharide.

Certain embodiments may comprise a therapeutic system. Non-limiting examples of therapeutic systems include, Lialda®, Mezavant®, Mesavanc®, Zacol NMX®, UCERIS®, Rifamycin SV MMX®, Methylene Blue MMX®, Pentasa®, PLGA nanoparticles, liposomes, EUDRATEC® COL, and self-microemulsifying drug delivery system (SMEDDS). Other therapeutic systems may be possible.

In some embodiments, the wt % of the therapeutic agent relative to the total weight of the article (e.g., a tablet, a capsule) is greater than or equal to 10 wt %, greater than or equal to 15 wt %, greater than or equal to 20 wt %, greater than or equal to 25 wt %, greater than or equal to 30 wt %, greater than or equal 40 wt %, greater than or equal to 50 wt %, greater than or equal to 60 wt %, greater than or equal to 70 wt %, greater than or equal to 75 wt %, greater than or equal to 80 wt %, greater than or equal 90 wt %, or greater than or equal to 95 wt %. In some embodiments, the wt % of therapeutic agent relative to the total weight of the article is less than or equal to 95 wt %, less than or equal to 90 wt %, less than or equal to 80 wt %, less than or equal to 75 wt %, less than or equal to 70 wt %, less than or equal to 60 wt %, less than or equal to 50 wt %, less than or equal to 40 wt %, less than or equal to 30 wt %, less than or equal to 25 wt %, less than or equal to 20 wt %, less than or equal to 15 wt %, or less than or equal to 10 wt %. Combinations of the above-references ranges are also possible (e.g., greater than or equal to 10 wt % and less than or equal to 50 wt %). Other ranges are possible.

In some embodiments, the amount (e.g., the mass) of the therapeutic agent present in the article (e.g., in a capsule, in a tablet) is greater than or equal to 10 mg, greater than or equal to 20 mg, greater than or equal to 25 mg, greater than or equal to 30 mg, greater than or equal to 50 mg, greater than or equal to 60 mg, greater than or equal to 70 mg, greater than or equal to 75 mg, greater than or equal to 80 mg, greater than or equal to 90 mg, greater than or equal to 95 mg, greater than or equal to 100 mg, greater than or equal to 250 mg, greater than or equal to 500 mg, greater than or equal to 750 mg, greater than or equal to 1 g, greater than or equal to 2 g, greater than or equal to 3 g, greater than or equal to 4 g, greater than or equal to 5 g, greater than or equal to 6 g, greater than or equal to 7 g, greater than or equal to 8 g, greater than or equal to 9 g, or greater than or equal to 10 g. In some embodiments, the amount of the secretion-inducing agent is less than or equal to 10 g, less than or equal to 9 g, less than or equal to 8 g. less than or equal to 7 g, less than or equal to 6 g, less than or equal to 5 g, less than or equal to 4 g, less than or equal to 3 g, less than or equal to 2 g, less than or equal to 1 g. less than or equal to 750 mg, less than or equal to 500 mg, less than or equal to 250 mg, less than or equal to 100 mg, less than or equal to 95 mg, less than or equal to 90 mg, less than or equal 80 mg, less than or equal to 75 mg, less than or equal to 70 mg, less than or equal to 60 mg, less than or equal to 50 mg, less than or equal to 40 mg, less than or equal to 30 mg, less than or equal to 25 mg, less than or equal to 20 mg, or less than or equal to 10 mg. Combinations of the above-referenced ranges are also possible (e.g., greater than or equal to 10 mg and less than or equal to 10 g). Other ranges are possible.

In some embodiments, a mass ratio of a secretion-inducing agent to a therapeutic agent is greater than or equal to 10:90, greater than or equal to 20:80, greater than or equal to 30:70, greater than or equal to 40:60, greater than or equal to 50:50, greater than or equal to 60:40, greater than or equal to 70:30, greater than or equal to 80:20, or greater than or equal to 90:10. In some embodiments, a mass ratio of a secretion-inducing agent to a therapeutic agent is less than or equal to 90:10, less than or equal to 80:20, less than or equal to 70:30, less than or equal to 60:40, less than or equal to 50:50, less than or equal to 40:60, less than or equal to 30:70, less than or equal to 20:80, or less than or equal to 10:90. Combinations of the above-referenced ranges are also possible (e.g., greater than or equal to 10:90 and less than or equal to 30:70). Other ranges are possible.

In some embodiments, a coating may be associated with the article. In certain embodiments, the coating is degradable and/or crodible (e.g., by gastrointestinal fluids under physiological conditions). In an exemplary set of embodiments, the degradable coating comprises an enteric polymer sold under the trademark EUDRAGIT® S100. Any suitable coating that is configured to release the secretion inducing agent to the desired portion of the gastrointestinal tract (such as in the distal portion of ileum or the distal part of the colon, as a non-limiting example) may be used. Non-limiting examples of suitable degradable coatings include enteric polymers sold under the trademark EUDRAGIT® S, enteric polymers sold under the trademark PHLORAL®, coatings associated with colon-targeted delivery systems (CODES), and enteric polymers sold under the trademark DUO-COAT®. In some embodiments, the coating is a crodible coating and comprises, for example, hydroxypropylmethyl cellulose (HPMC). Other crodible coatings are also possible.

Some embodiments of articles described herein may comprise additional components (e.g., excipients, coatings). In some embodiments, the additional component(s) may be unrelated to secretion production or therapeutic abilities. The additional components may, in some cases, help with stability of the article (e.g. a tablet, capsule, etc.), solubility of the article, and/or enhance the article's ability to deliver the therapeutic agent to the desired portion of the gastrointestinal tract (e.g. as a degradable and/or crodible coating). In some embodiments, the additional component comprises magnesium stearate. In some embodiments, the additional component comprises hydroxypropylmethyl cellulose. In some embodiments, the additional component comprises hydrophilic fumed silica sold under the trademark AEROSIL® 200 Pharma For some embodiments, additional components (e.g., excipients) may assist with forming a matrix (i.e., a surrounding material designed to hold the components of the article together, e.g., hold the components of an article into a tablet) around or within the article. In some embodiments, additional components may help control the release of components. Non-limiting examples of suitable matrix forming and/or release controlling agents include methylcellulose, hydroxypropylcellulose, hydroxypropylmethylcellulose, alginates, plant derived gums, chitosan, gelatin, pectin, carraganes, polyacrylates, polyethyleneoxides, and starch. Examples of hydrophobic matrix forming and/or release controlling agents include waxes, fatty acids, fatty alcohols and esters, glycerolesters, polyesteramide, ethylcellulose, polyethylene, polypropylene, polythiourethane, polyvinylbutyral, polylacticacid, poly(lactide-co-glycolide), celluloseacetate, and celluloseacetate butyrate. Other additional components that may assist with delivery of a secretion inducing or a therapeutic agent are also possible.

In some embodiments, the first portion, the second portion, and/or the additional component may comprise a hydrophilising agent. Non-limiting examples of suitable hydrophilising agents include cyclodextrins, surfactants, solid buffers (e.g. sodium citrate/citric acid). Other examples of hydrophilising agents are possible as the disclosure is not so limited.

Some embodiments may improve or enhance the motility of the gastrointestinal tract. As described herein, motility refers to the contraction of the muscles that mix and propel contents in the gastrointestinal (GI) tract. In some embodiments, the secretion inducing agent, such as a bile acid, may increase the motility of the colon, in addition to increasing gastrointestinal secretions. Increased motility of the colon may result in improved mixing of the therapeutic agent and hence may improve the dissolution and/or the absorption of the therapeutic agent.

Articles described herein may be configured into any form appropriate for administering the article to the gastrointestinal tract. In some embodiments, the article is configured into a tablet, a pill, or a capsule. In some embodiments, a degradable coating is associated with the article. Other forms of the article may be appropriate for administering to the gastrointestinal tract as the disclosure is not so limited.

In some embodiments, the methods and articles are administered to a subject (e.g., orally). In certain embodiments, the system may be administered orally, rectally, vaginally, nasally, or uretherally. In certain embodiments, upon reaching a location internal to the subject (e.g., the gastrointestinal tract), at least a portion of a coating degrades such that a secretion inducing agent makes contact with a tissue located internal to the subject. In some embodiments, contact with a tissue stimulates the release of intestinal fluids. In some embodiments, the location internally of the subject is the colon, the duodenum, the ileum, the jejunum, the stomach, or the esophagus. As described above and herein, in some embodiments, a therapeutic agent may be released during and/or after penetration of the tissue located internal to the subject. In some embodiments, the secretion inducing agent promotes secretion only in desired portions along the gastrointestinal tract, such as only along the caecum or other parts of the ascending colon, as non-limiting examples. In some such embodiments, such targeted secretion may advantageously transiently initiate the release of the therapeutic agent, rather than along the entire gastrointestinal tract. In some embodiments, release of the therapeutic agent may be selectively released along only desired portions of the GI tract or the colon.

In certain embodiments, articles and methods are administered in the gastrointestinal tract. For example, in some embodiments, a secretion inducing agent and/or a therapeutic agent are configured to be released in a colon of a subject. In some cases, the secretion inducing agent is released within one-fifth of the distance between the ilcocecal valve and the hepatic flexure. Other areas along the gastrointestinal tract are also possible as the disclosure is not intended to be so limiting.

Some embodiments are configured to release a secretion inducing agent to the gastrointestinal tract. The secretion inducing agent, in some embodiments, stimulates the release of additional intestinal fluids (e.g. water, enzymes, hormones, proteins etc.) such that there is more intestinal fluid present with the secretion inducing agent present compared to with the absence of a secretion inducing agent. As described herein, intestinal fluid describes the clear to pale yellow watery secretions from the glands lining the colon. The additional secretions caused by the secretion inducing agent may enhance the solubility or availability of a therapeutic agent so that it may be better utilized by a subject. In some embodiments, the additional secretions released as a result of the secretion inducing agent may contain more water relative to secretions induced in the proximal portions of the GI tract. In some such embodiments, this may advantageously enhance the dissolution and/or the solubility of the therapeutic agent. In some embodiments, the additional secretions released as a result of the secretion inducing agent may contain less digestive enzymes relative to secretions induced in the proximal portions of the GI tract. This may advantageously allow for a therapeutic agent that might normally degrade due to digestive enzymes in the proximal GI tract to persist longer along the GI tract and provide a therapeutic effect further along the GI tract. In some embodiments, the release of additional intestinal fluids may promote the release of more secretion inducing agent, such that a positive feedback loop is provided. For example, without wishing to be bound by theory, in some cases the secretion inducing agent may promote the release of intestinal fluids, which may in turn promote the release of additional secretion inducing agent, which may then promote the release of more intestinal fluids (e.g., as compared to the release of intestinal fluids without the secretion inducing agent).

For certain embodiments, the secretion inducing agent may be present along the gastrointestinal tract with a local concentration of at least 3 mM. In some embodiments, the local concentration of the secretion inducing agent is at least 5 mM. That is to say, in some embodiments, the degradable coating releases the secretion inducing agent to produce a local internal concentration of the secretion inducing agent e.g., of at least 3 mM or at least 5 mM at a location internal to the subject. In some embodiments, the secretion inducing agent is released such that a local internal concentration of at least 3 mM, at least 5 mM, at least 10 mM, at least 15 mM, at least 20 mM, at least 30 mM, or at least 50 mM is produced. In some embodiments, the secretion inducing agent is released such that a local internal concentration of less than or equal to 100 mM, less than or equal to 50 mM, less than or equal to 30 mM, less than or equal to 20 mM, less than or equal to 15 mM, less than or equal to 10 mM, or less than or equal to 5 mM is produced. As described herein, "local concentration" refers to the amount of substance per unit volume at a position nearby the article. For example, the concentration of the secretion inducing agent along the entirety of the gastrointestinal tract may be substantially less than 3 mM, but the concentration of the secretion inducing agent in the vicinity of an article configured to release the secretion inducing agent may be equal to or greater than 3 mM.

Certain embodiments of the article are configured into a form suitable for administering orally to a subject, such as a pill, a tablet, or a capsule. In some embodiments, the size of the article may conform (e.g., fit within) with standard capsule sizes known in the art, such as 000, 00, 0, 1, 2, 3, or 4.

In certain embodiments, an article configured for release of a therapeutic agent may have a largest cross-sectional dimension (e.g. a diameter) of at least 10 mm, at least 12 mm, at least 14 mm, of at least 15 mm, of at least 18 mm, of at least 19 mm, of at least 21 mm, of at least 23 mm, or of at least 26 mm. In some embodiments, an article configured for release of a therapeutic agent may have a largest cross-sectional dimension of at most 27 mm, of at most 24 mm, of at most 22 mm, of at most 20 mm, of at most 18 mm, of at most 16 mm, of at most 15 mm, or of at most 10 mm.

Some embodiments may be configured to eliminated, reduce, or minimize abdominal pain and/or other adverse effects. For example, some secretion inducing agents (e.g. bile acids) may cause adnominal discomfort when released in certain locations along the gastrointestinal tract. Traditional capsules may, in some cases, lead to a burst release of CDC (e.g., resulting in massive phasic contractions in a subject, resulting in abdominal pain. However, as described herein some embodiments, the delivery system described may advantageously control the release of the secretion inducing agent such that it is released only in certain parts of the gastrointestinal tract, thereby reducing or eliminating abdominal pain. In this way, abdominal pain to a subject may be avoided or mitigated.

Exemplary Embodiments

In one aspect, an article configured for release of a therapeutic agent in a colon of a subject is described. In some embodiments, the article comprises a first portion comprising a secretion inducing agent and a second portion, adjacent to the first portion, where the second portion comprises a therapeutic agent. Certain embodiments of the article may also be configured with a degradable coating.

In certain aspects, an article configured to release a therapeutic agent in a portion of an intestine of a subject is described. Some embodiments of the article comprise a first component configured to increase the amount of intestinal fluid present in the intestine of the subject and a second component associated with the first component configured to release a therapeutic agent in the intestine of the subject.

In another aspect, a method of intestinal drug delivery is described. The method comprises exposing a portion of an intestine of a subject to an intestinal secretion inducing agent such that the intestine is induced to release intestinal fluids. In some embodiments, the method provides a therapeutic agent to a portion of a intestine of the subject such that the secretion inducing agent increases the amount of the therapeutic agent available for absorption by the intestine of the subject.

In yet another aspect, a method for administering an article, comprising a therapeutic agent, to a subject is described. In some embodiments, the method comprises administering an article to the subject and releasing a therapeutic agent from the article to a small intestine of the subject. Certain embodiments of the method use an article that comprises a first portion comprising a secretion inducing agent; a second portion, adjacent to the first portion, comprising the therapeutic agent; and a degradable coating associated with the article. In some embodiments, the secretion inducing agent is configured to increase the amount of intestinal fluid present in a small intestine of the subject.

EXAMPLES

The following examples are intended to illustrate certain embodiments of the present invention, but do not exemplify the full scope of the invention.

Example 1

This example describes the fabrication and testing of an exemplary tablet for delivery of a therapeutic agent, in accordance with certain embodiments.

The system consists of an article (e.g., a tablet) having a two-layer core and an Eurdragit S100 coating. The first, extended release, layer comprises 81% Na-CDC, 17% Hydroxypropylmethyl cellulose (MW: 120.000) and 2% magnesium stearate. The second, boost release, layer comprises 98% Na-CDC and 2% magnesium stearate. Two-layer tablets (10 mm diameter) were compressed using a NP-RD10A tablet press from Natoli (Force: 20,000 N). Each pill contains a booster layer of 98 mg and an extended release layer of 400 mg Na-CDC. The tablets were coated with EUDRAGIT® S100 coating following the manufacturer's recommendations. Briefly, EUDRAGIT® S100 coating solution was prepared by dissolving and homogenizing EUDRAGIT® S100, magnesium stearate and triethyl citrate in a solvent mixture composed of water, acetone and isopropanol. The tablets were spray-coated using an Erweka AR403 pan coater.

Control experiments were performed using capsules prepared by filling 1 g of Na-CDC into a gelatin capsules. The capsules were coated by dip coating using EUDRAGIT® S100.

Dissolution experiments were performed using a Hanson Vision dissolution testing system. Dissolution was assessed in 800 mL phosphate buffer (0.2M, pH 6.8 formulation, 37C, stirred at 50 rpm). After 2 hours pH was changed to 7.4 (2 M NaOH).

Figure 7A:
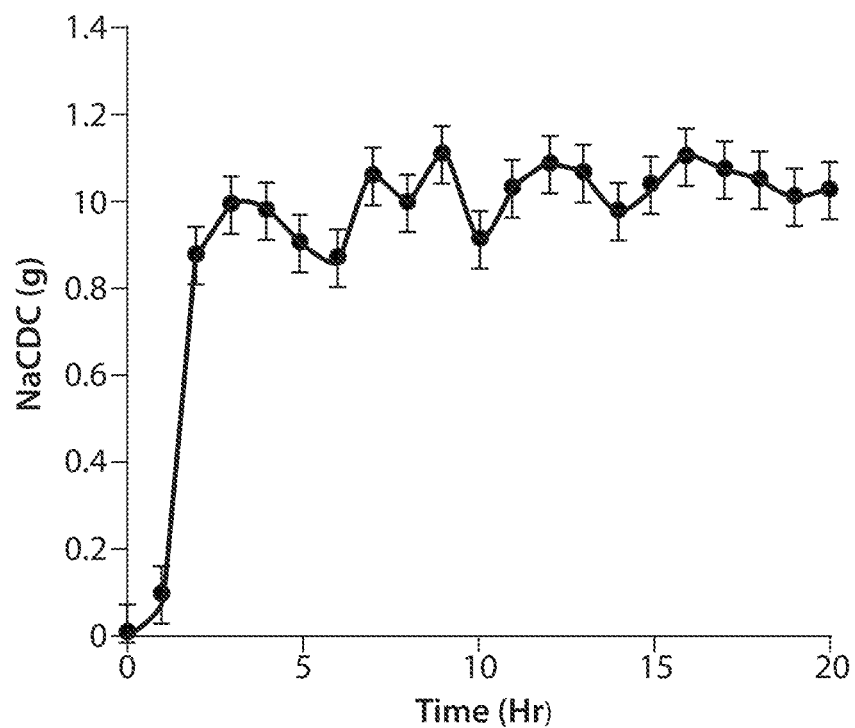
FIG. 7A shows in vitro dissolution profiles for exemplary bilayer delivery systems, according to one set of embodiments.
Figure 7B:
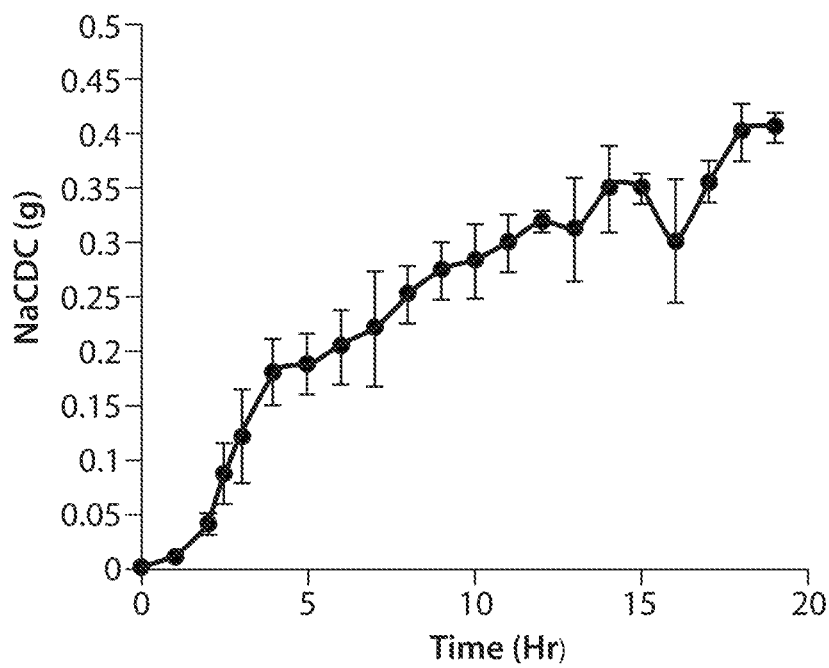
FIG. 7B shows in vitro dissolution profiles for exemplary bilayer delivery systems, according to one set of embodiments.

The release kinetics of the delivery system was assessed in comparison to the clinical reference product (1 g Na-CDC capsules coated with EUDRAGIT® S 100, FIGS. 7A-7B). To simulate passage through the gastrointestinal tract release was assessed in phosphate buffer (pH 6.8) for two hours and pH 7.4. Na-CDC release from the clinical reference product plateaus after 2 hours. Drug release from delivery system is detectable after 2 hours and a total of 70 mg Na-CDC is released within the first 30 minutes. Thereafter controlled Na-CDC release follows zero order kinetics for 20 hours. Swellable HPMC within the delivery system facilitates a pH independent release mechanism (FIG. 8) shows the inflow of medium into the system induces swelling which promotes diffusion of Ca-CDC through the coating layer.

Example 2

This example describes the fabrication and testing of an exemplary tablet for delivery of a therapeutic agent, in accordance with certain embodiments.

FIG. 7 shows the in-vitro dissolution profile of a capsule filled with 1 g Na-CDC (EUDRAGIT® S100 coated) FIG. 10 A) shows the in vitro dissolution profile of delivery systems comprising 0.5 g Na-CDC (EUDRAGIT® S100 coated). The systems where immersed in Simulated Gastric Fluid (SGF, 1 h) and in 0.2M phosphate buffer ("intestinal fluid", pH 6.8, 1 h) before pH was adjusted to 7.4 (2 M NaOH) after another hour. The single layered delivery system demonstrates the release profile of a formulation containing only the "therapeutic drug layer" (0.5 g NaCDC/HPMC) without the "booster layer". In-vivo pharmacokinetic profile in swine of B) The capsule (A),C) 2 delivery system (bilayer) and D) 2 single layered delivery systems demonstrating extended release in vivo. Increased chenodeoxycholic acid (CDCA) serum levels in the bilayer group as compared to the single layered group demonstrates increased dissolution in accordance with certain embodiments. In vitro dissolution experiments (FIG. 10A) were performed using a Hanson (Chatsworth, CA) Vision dissolution testing system (37C, stirred at 100 rpm). The delivery systems were exposed to 800 mL Simulated Gastric Fluid (SGF, without enzymes, USP) for one hour, before the systems were transferred to Simulated Intestinal Fluid for 1 hour (SIF, without enzymes, pH 6.8). After 1 hour the pH was adjusted to 7.4 (2 M NaOH).

Example 3

The following example demonstrates the administration of an article described herein.

Without wishing to be bound by theory, burst release of Chenodeoxycholate (CDC) from a traditional capsule can trigger massive contractions which the patient feels as abdominal pain. This was previously shown for bile acids in man at a concentration over 3 mM.

Figure 4:
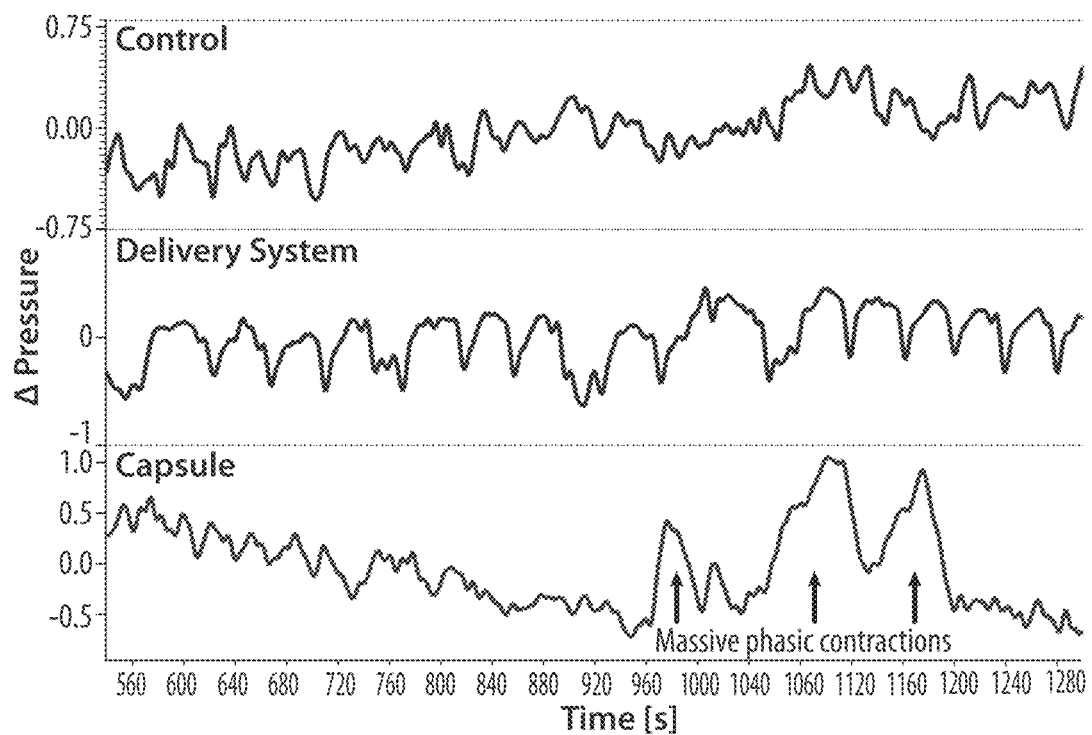
FIG. 4 shows a plot of change in intrarectal pressure versus time, according to one set of embodiments.

Intrarectal pressure was measured following rectal placement of the traditional CDC "capsule" and the bilayered "delivery system" (e.g., an article as described herein) along with 50 mL saline. The capsule is 1 g NaCDC (the "capsule"). The bilayered "delivery system" described here used 0.5 g NaCDC. As shown in FIG. 4, massive contractions in pigs were observed in pigs receiving the capsule but not in those receiving the delivery system or not receiving delivery systems (control).

Example 4

The following example demonstrates exemplary configurations of various articles, described herein.

Figure 5:
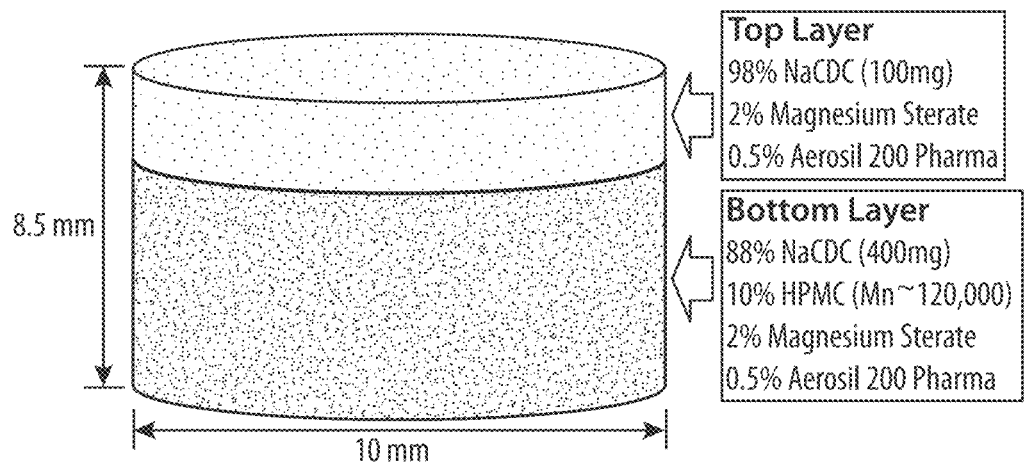
FIG. 5 shows a schematic diagram of an exemplary article, according to one set of embodiments.
Figure 6:
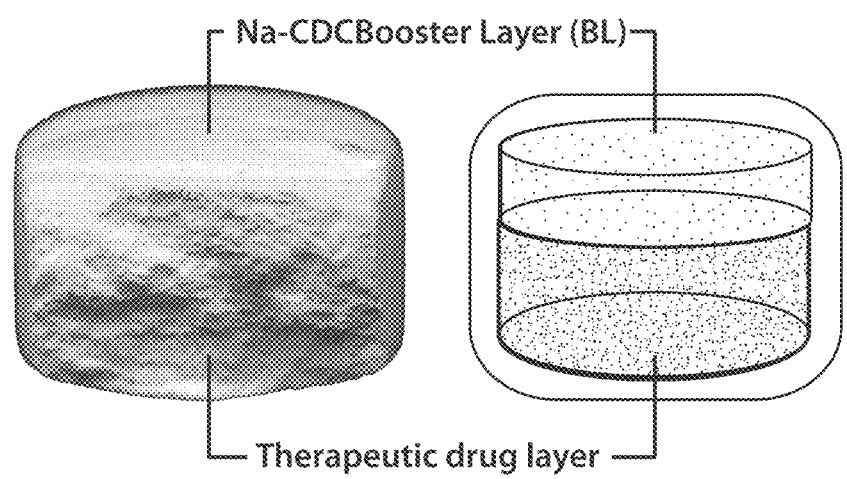
FIG. 6 shows a schematic diagram of an exemplary article, according to one set of embodiments.

FIGS. 5-6 show an exemplary capsule manufactured as described herein.

The first portion may comprise about 98% NaCDC as a secretion inducing agent and about 2% and 0.5% magnesium stearate and Aerosil® 200 Pharma, respectively, as additional components or excipientsThe second portion may comprise about 88% NaCDC, 10% HPMC, 2% magnesium stearate, and 0.5% Aerosil® 200 PharmaIn some embodiments, the total amount of NaCDC is 500 mg. In some embodiments, the weight of an article (e.g. a pill) is about 557 mg.

Figure 8A:
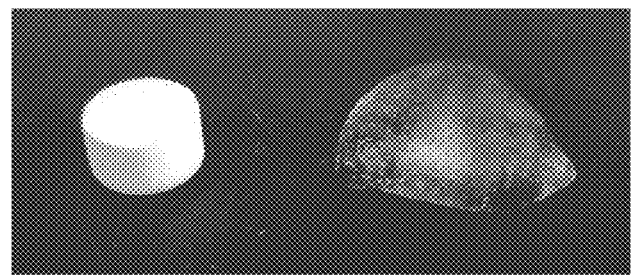
FIG. 8A shows exemplary bilayer delivery system before and after release, according to one set of embodiments.
Figure 8B:
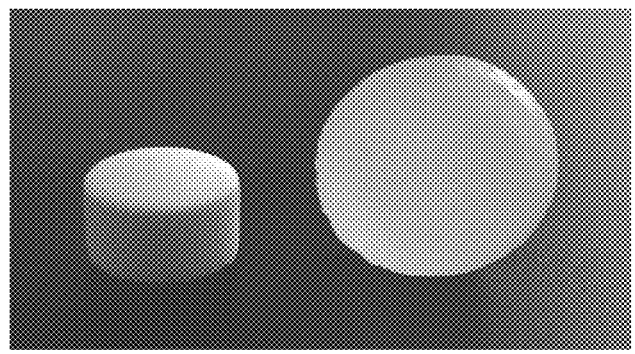
FIG. 8B shows exemplary bilayer delivery system before and after release, according to one set of embodiments.
Figure 9:
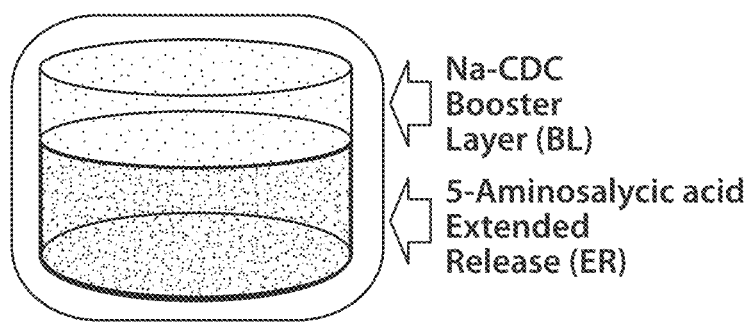
FIG. 9 shows a schematic illustration of an article configured to release NaCDC as the secretion inducing agent and 5-aminosalycic acid as the therapeutic agent, according to one set of embodiments.

FIGS. 8A-8B are photographs of exemplary articles, as described herein. FIG. 9 is a schematic illustration of an exemplary article comprising a Na-CDC layer and a 5-aminosalycic acid layer.

Figure 10A:
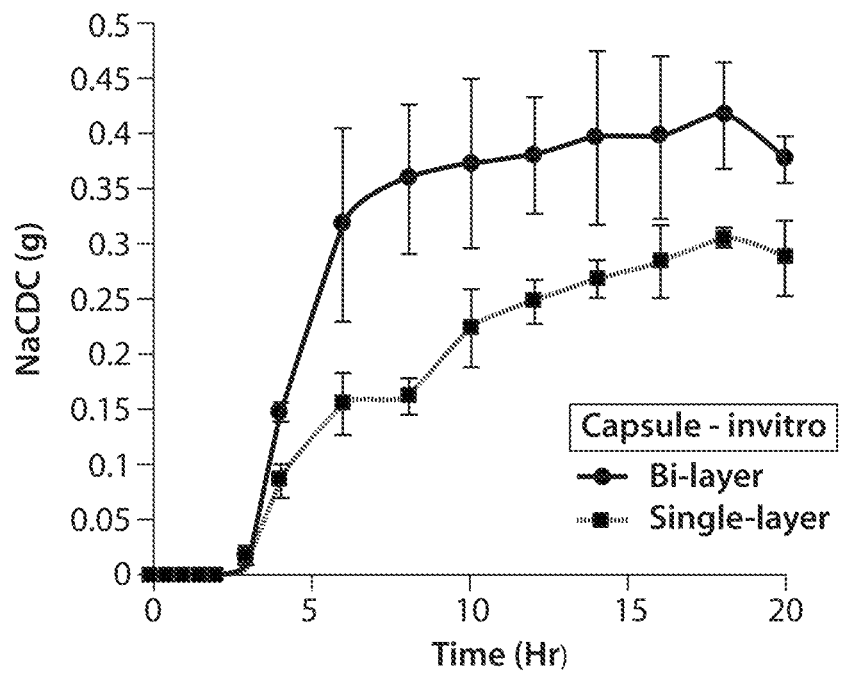
FIG. 10A shows the release profile over time for a traditional capsule and a traditional controlled release delivery system ("single layered") versus articles described herein ("bilayer"), according to one set of embodiments.

FIG. 10A is a plot of dissolution of NaCDC (g) versus time for traditional capsules (FIG. 7A) versus the inventive articles described herein.

Figure 10B:
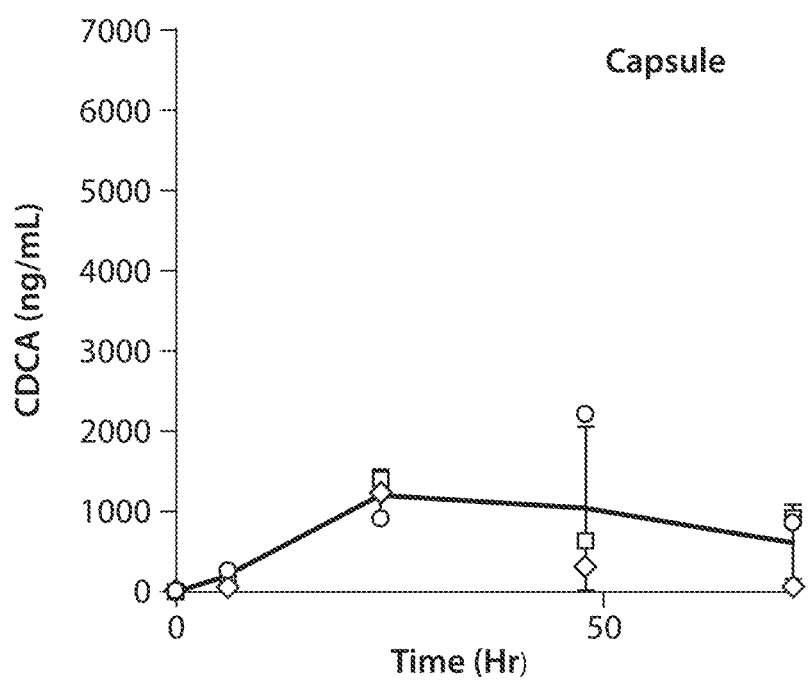
FIG. 10B shows the release profile over time for a traditional capsule and a traditional controlled release delivery system ("single layered") versus articles described herein ("bilayer"), according to one set of embodiments.
Figure 10C:
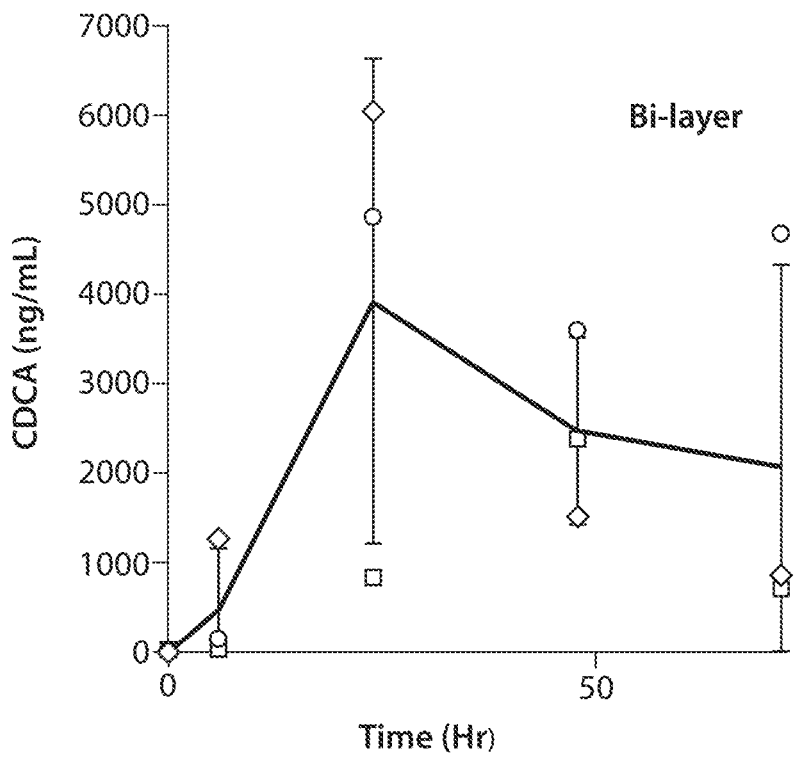
FIG. 10C shows the release profile over time for a traditional capsule and a traditional controlled release delivery system ("single layered") versus articles described herein ("bilayer"), according to one set of embodiments.
Figure 10D:
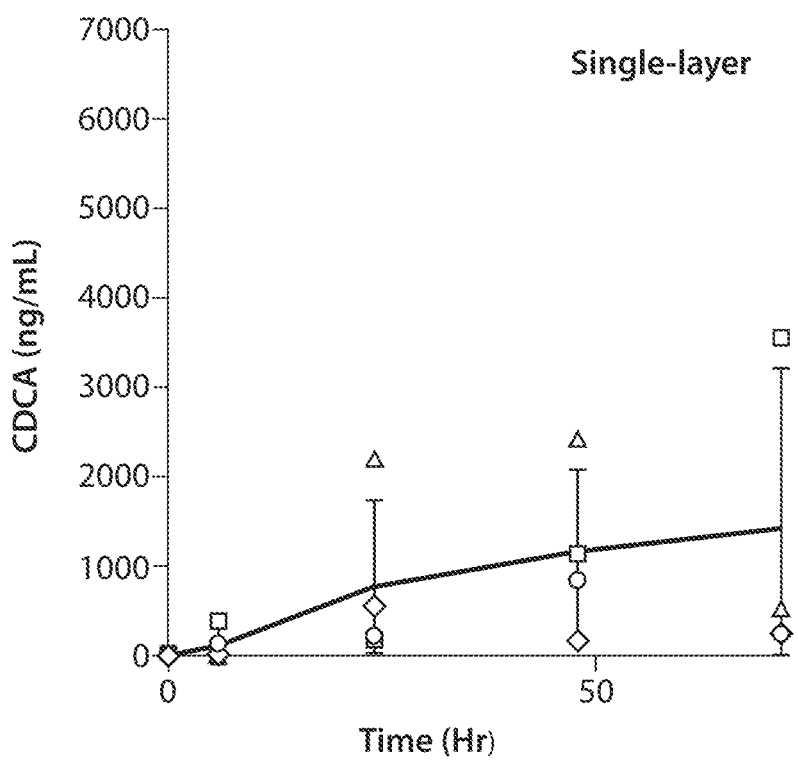
FIG. 10D shows the release profile over time for a traditional capsule and a traditional controlled release delivery system ("single layered") versus articles described herein ("bilayer"), according to one set of embodiments.
Figure 11A:
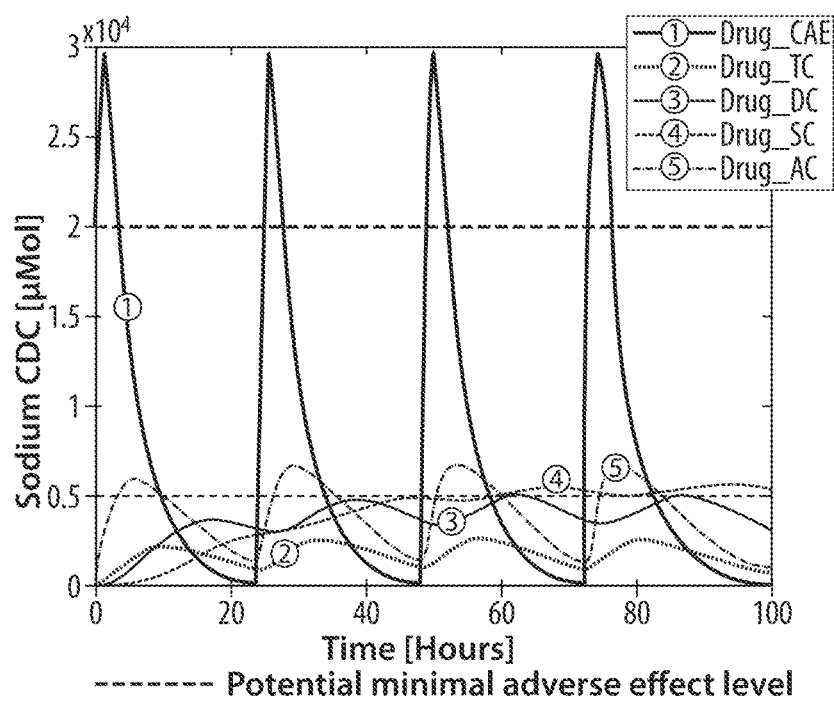
FIG. 11A shows modeled colonic Na-CDC concentration delivered as delayed bolus as described in conventional drug delivery systems and delayed and extended release with first order release kinetics, according to certain embodiments.
Figure 11B:
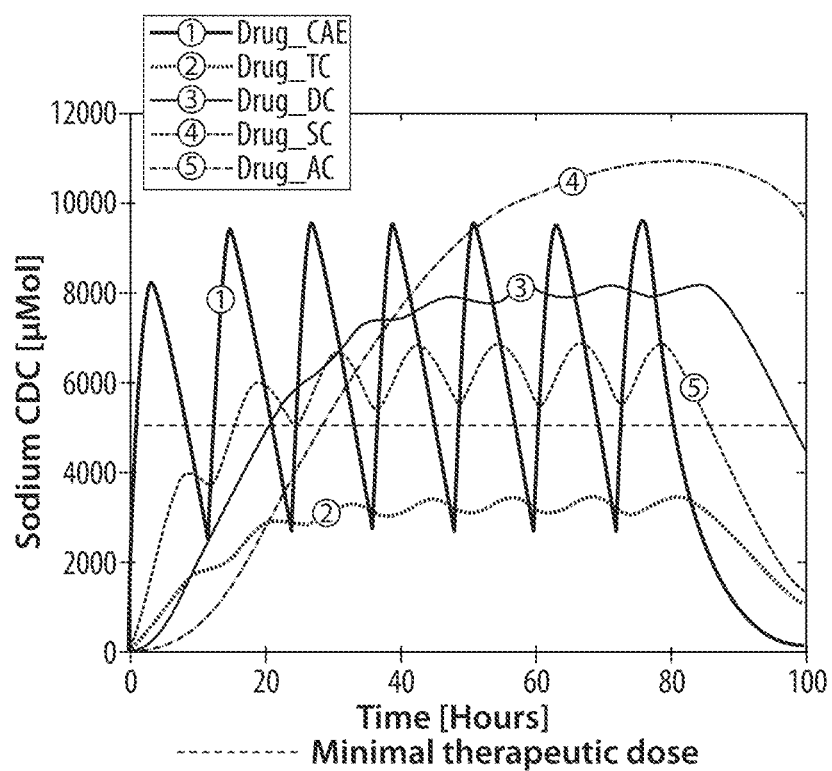
FIG. 11B shows modeled colonic Na-CDC concentration delivered as delayed bolus as described in conventional drug delivery systems and delayed and extended release with first order release kinetics, according to certain embodiments.

FIGS. 10B-D are plots of pharmacokinetic profiles of NaCDC versus time for traditional capsules (FIG. 7A) and traditional controlled release system (single layered) versus the inventive article described herein.

Example 5

The following example describes exemplary in vivo porcine studies using various articles, described herein.

All procedures were conducted in accordance with protocols approved by the Massachusetts Institute of Technology Committee on Animal. Twelve separate female Yorkshire pigs weighing approximately 30-50 kg were randomly assigned for in vivo evaluation. Following overnight fasting, the animals were sedated with Telazol (tiletamine/zolazepam) 5 mg/kg, xylazine 2 mg/kg, and atropine 0.04 mg/kg. Endotracheal intubation was performed, and anesthesia was maintained with isoflurane thereafter (1-3% in oxygen). For pharmacokinetic studies, the delivery systems were placed into the small intestine by using an esophageal overtube (US Endoscopy, Mentor, OH) with endoscopic guidance. Blood was sampled through a central venous catheter or through mammal bleeds in case catheter placement was not possible.

CDCA in serum from these in vivo experiments were analyzed using Ultra-Performance Liquid Chromatography-Tandem Mass Spectrometry (UPLC-MS/MS).

Analysis was performed on a Waters ACQUITY UPLC®-I-Class System aligned with a Waters Xevo® TQ-S mass spectrometer (Waters Corporation, Milford MA). Liquid chromatographic separation was performed on an Acquity UPLC® HSS T3 (50 mm×2.1 mm, 1.8 μm particle size) column at 50° C. The mobile phase consisted of aqueous 0.1% formic acid, 10 mM ammonium formate solution (Mobile Phase A) and acetonitrile: 10 mM ammonium formate, 0.1% formic acid solution (95:5 v/v) (Mobile Phase B). The mobile phase had a continuous flow rate of 0.6 mL/min using a time and solvent gradient composition.

For the analysis of CDCA, the initial composition, 95% Mobile Phase A, was held for 1.00 minutes, following which the composition was changed linearly to 2% Mobile Phase A until 1.80 minutes. The composition of 2% Mobile Phase A and 98% Mobile Phase B was held constant until 3.00 minutes. The composition linearly changed to 80% Mobile Phase A at 3.50 minutes and was linearly returned to 95% Mobile Phase A until completion of the run, ending at 4.50 minutes, where it remained for column equilibration. The total run time was 4.50 minutes. The mass to charge transitions (m/z) used to quantitate CDCA was 391.452>391.591. For internal standard, d-4 CDCA, 395.38>396.07 m/z transition was used for quantitation.

Sample introduction and ionization was by electrospray ionization (ESI) in the positive ionization mode. Waters MassLynx 4.1 software was used for data acquisition and analysis. Stock solutions were prepared in methanol at a concentration of 500 µg/mL. A twelve-point calibration curve was prepared in analyte-free, blank serum ranging from 1.25-5000 ng/mL. 100 µl of each serum sample was spiked with 200 µl of 250 ng/mL internal standard in acetonitrile to elicit protein precipitation. Samples were vortexed, sonicated for 10 minutes, and centrifuged for 10 minutes at 13,000 rpm. 200 µl of supernatant was pipetted into a 96-well plate containing 200 µl of water. Finally, 10.00 µl was injected onto the UPLC-ESI-MS system for analysis. One serum sample was lost (72 h, single layered) and we included a fourth animal for this group.

CDCA concentrations were then analyzed utilizing an Agilent (Santa Clara, CA) 1260 Infinity II HPLC system equipped with an Agilent 6120B mass spectrometer. Data processing and analysis was performed using OpenLab CDS ChemStation (Agilent). Isocratic separation was achieved using an Agilent 4.6×50 mm EC C-18 Poroshell column with 2.7 µm particles, maintained at 55° C. The mobile phase consisted of 20% 10 mM ammonium acetate in water (unbuffered) and 80% methanol using a flow rate of 0.850 mL/min over a period of 6 minutes. Gradient separation was achieved over a 5 min run time (3 min post run). The injection volume was 5 µL, and the selected ultraviolet (UV) detection wavelength was 210 nm at an acquisition rate of 5 Hz. The ESI drying gas flow rate and temperature was 10 L/min and 350° C., accordingly. The SIM of CDC and CA internal standard were analyzed using negative mode electron spray ionization at a gain of 2.00, fragmentor of 70, monitoring mass-to-charge ratios of 391.40 m/z and 408.60 m/z, respectively.

Disintegration of bilayer systems in vivo was profiled in a terminal procedure in swine. After sedation and intubation with isoflurane, a laparotomy was performed using a ventral middle line incision from the xiphoid to the pubis. The delivery systems were then placed through an incision into the duodenum and retrieved 4 hours later. A set of unrelated different experiments were performed concurrently during the terminal procedure but did not interfere with the GI tract either physically nor pharmacologically.

Figure 12A:
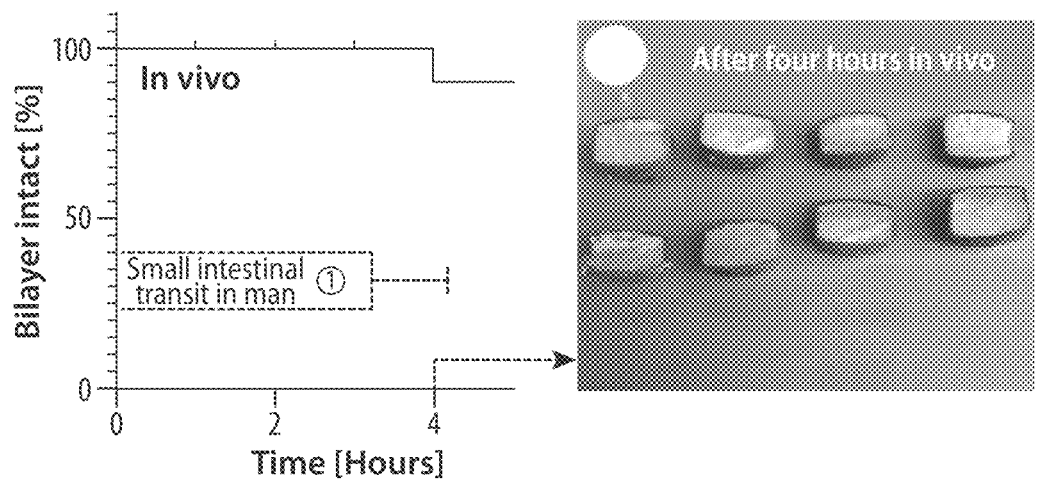
FIG. 12A shows in vivo evaluation of CDC bilayer delivery systems as compared to the capsule formulation using a Kaplan Meyer plot demonstrating the bilayer delivery system's capacity to maintain integrity throughout intestinal passage in swine and a retrieved dissected delivery systems after 4 hours, according to one set of embodiments.
Figure 12B:
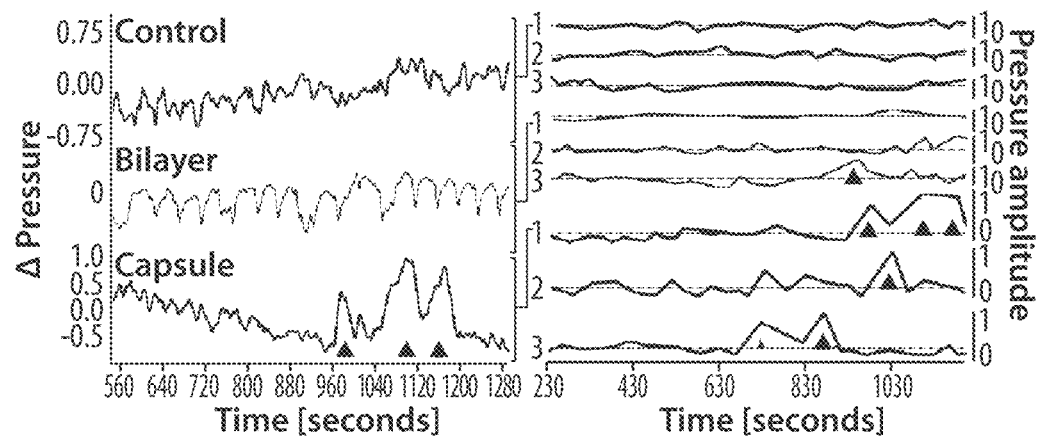
FIG. 12B shows representative rectal manometry patterns following rectal placement of uncoated bilayer delivery systems or CDC capsules with amplitudes of three rectal manometry patterns and giant contractions indicated by arrowheads (data normalized to the mean amplitude), according to one set of embodiments.
Figure 13A:
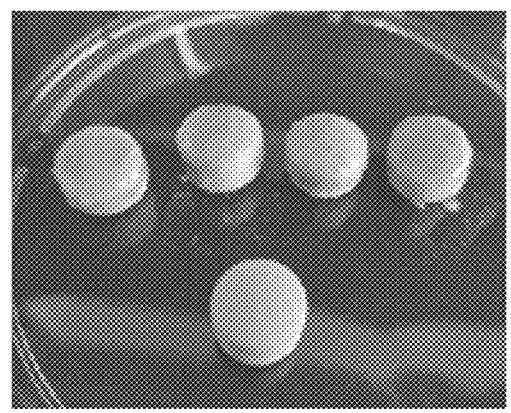
FIG. 13A is a photographic image of bilayered delivery systems retrieved from the small intestine of a terminal pig model where a black arrow indicates one out of the twelve delivery systems disintegrated after 4 hours while the rest remained intact, according to one set of embodiments.
Figure 13B:
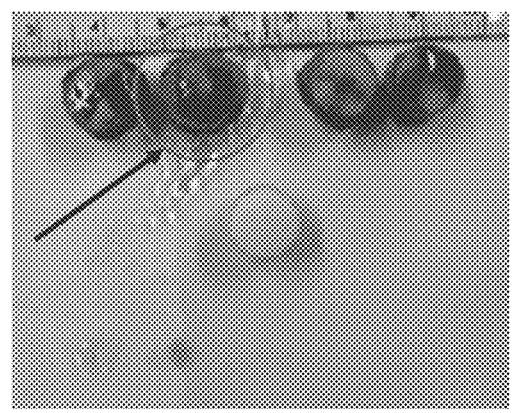
FIG. 13B is a photographic image of bilayered delivery systems retrieved from the small intestine of a terminal pig model where a black arrow indicates one out of the twelve delivery systems disintegrated after 4 hours while the rest remained intact, according to one set of embodiments.
Figure 13C:
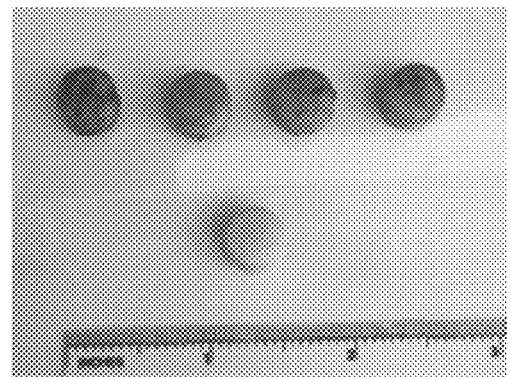
FIG. 13C is a photographic image of bilayered delivery systems retrieved from the small intestine of a terminal pig model where a black arrow indicates one out of the twelve delivery systems disintegrated after 4 hours while the rest remained intact, according to one set of embodiments.

To understand in vivo disintegration characteristics of the delivery system, the release systems were retrieved following intestinal passage in swine during a terminal procedure. 91.6% (11 systems) of the release systems placed into the SI (12) remained intact until retrieval 4 hours after implantation (FIGS. 12A-12B, FIG. 13; see FIG. 13B for partly disintegrated system).

Example 6

The following example describes exemplary rectal manometry of various articles described herein to assess rectal motility.

The effect of bile acid formulations on rectal motility was analyzed. Therefore, the rectum was cleaned with ~120 mL saline infused through a Foley catheter. One uncoated CDC capsule or one uncoated bilayer delivery system was applied rectally along with 50 mL saline before measurement was started. No CDC was applied in the control group. The measurement was done by rectal placement of an air inflated balloon connected (PVC tube) to a micro pressure sensor (MPRLS, Honeywell Charlotte, NC). The sampling frequency of the was 30 Hz. An ultralow band pass Finite Impulse Response (FIR) filter was used (MATLAB, MathWorks, Natick, MA) with cutoff frequency of 0.1 Hz, to filter auxiliary signals (respiration) and identify rectal motility.

A clinical challenge of colonic CDC delivery is noticeable abdominal cramping and pain in patients. It was hypothesized that this symptom was due to massive contractions triggered by local super-physiological CDC levels within the proximal colon. Thus rectal manometry was performed following placement of uncoated CDC capsules and bilayer systems in comparison to the control receiving no treatment. Approximately 15 minutes after rectal application, repeated massive contractions in all pigs receiving CDC capsules by measuring the pressure variation in colon (FIG. 12C). FIG. 12D shows the unified and filtered colon pressure variation by means of a low pass filter. In the group receiving the bilayer system, only one major contraction was observed. In the control group no massive contractions were observed.

Example 7

The following example describes exemplary in vitro and in silico studies of various articles described herein.

Dissolution experiments were performed using a Hanson (Chatsworth, CA) Vision Elite 8 dissolution testing system (37° C., stirred at 100 rpm). The delivery systems were exposed to 800 mL of Simulated Gastric Fluid (SGF, without enzymes, USP) for one hour, before transferring to Simulated Intestinal Fluid for 1 hour (SIF, without enzymes, pH 6.8). After one hour, the pH was adjusted to 7.4 (2 M NaOH). In another set of experiments, the CDC capsules and bilayer pills were exposed to SIF (pH 6.8, 1 hour) for one hour before they were transferred to SIF (pH 7.4). These experiments were performed at 50 rpm under otherwise identical conditions.

For pharmacokinetic in silico simulations, Symbiology from Math Works (Natick, MA) was used to generate a five-compartment gastrointestinal model (see Supplementary FIG. 2 for setup). The compartments modeled were the caecum, ascending colon, transverse colon, descending colon, and sigmoid. First-order kinetics were assumed for all reactions. For parametric data, a one-way ANOVA following post-hoc Duncan test was used. A p≤0.05 was considered statistically significant.

| Part | Volume [mL] | Half transit time [hour] | Rate [hour$^{-1}$] (=K) |
|---|---|---|---|
| Caecum (CAE) | 50 | 1 | 0.693 |
| Ascending colon (AC) | 203 | 2.5 | 0.277 |
| Transverse colon (TC) | 198 | 2.9 | 0.239 |
| Descending colon (DC) | 160 | 5.5 | 0.126 |
| Sigmoid (SC) | 250 | 12.1 | 0.057 |

Figure 14A:
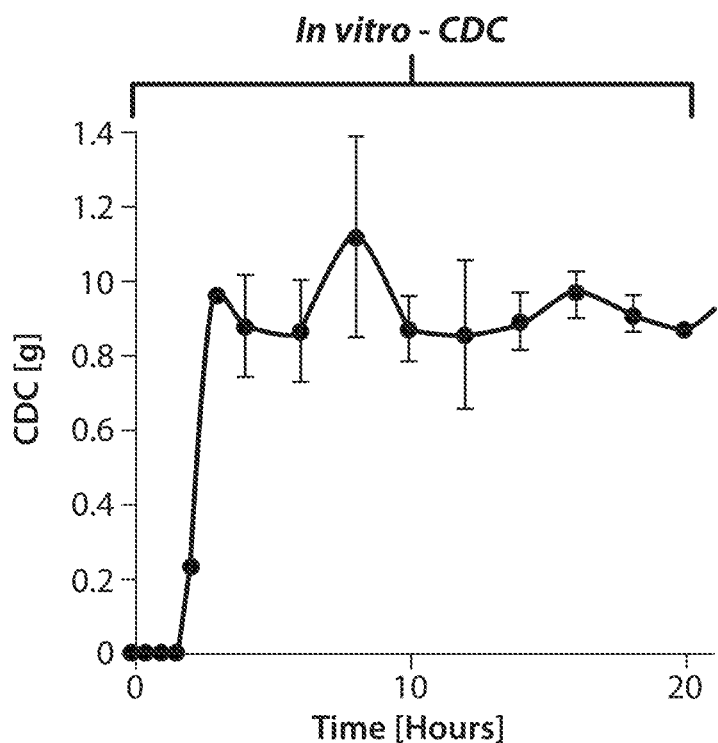
FIG. 14A shows pharmacokinetic evaluation of the bilayer delivery system versus traditional formulations using in vitro and in silico data, according to one set of embodiments.
Figure 14B:
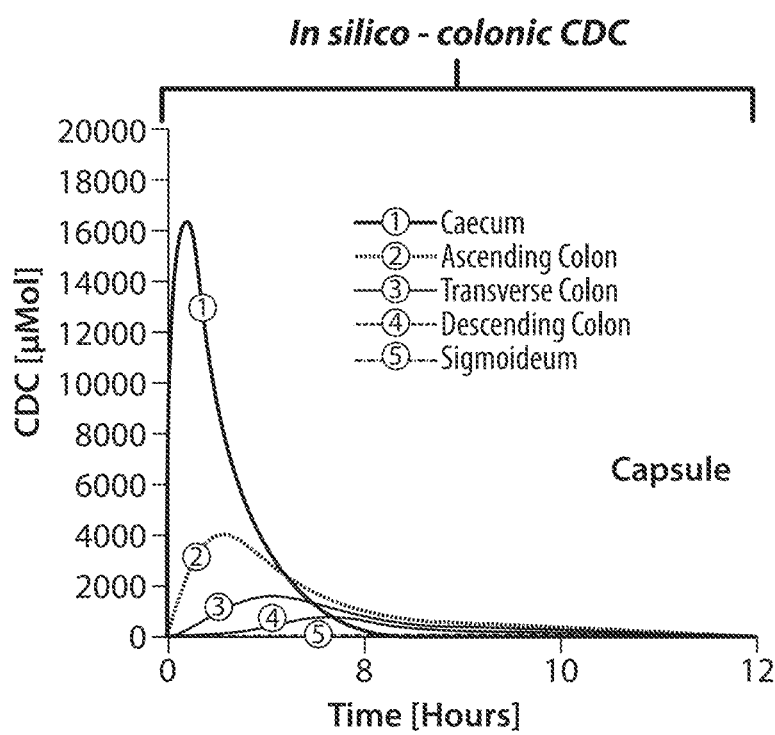
FIG. 14B shows pharmacokinetic evaluation of the bilayer delivery system versus traditional formulations using in vitro and in silico data, according to one set of embodiments.
Figure 14C:
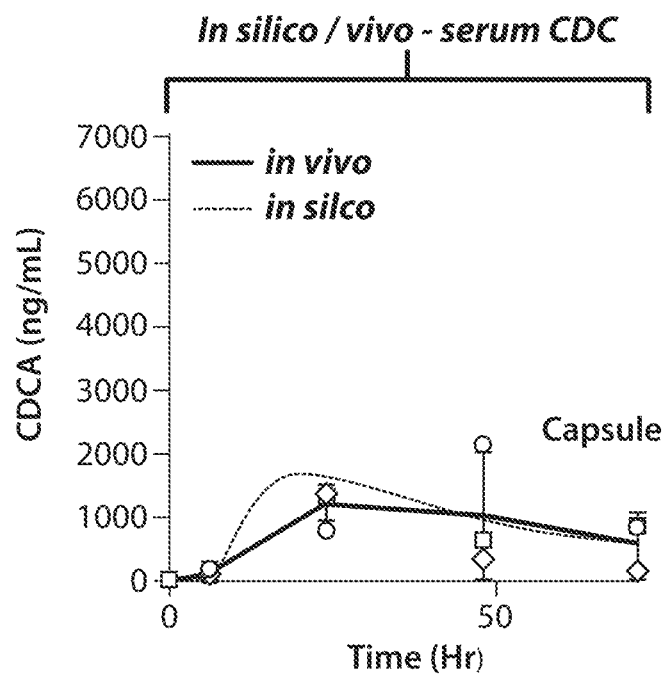
FIG. 14C shows pharmacokinetic evaluation of the bilayer delivery system versus traditional formulations using in vitro and in silico data, according to one set of embodiments.
Figure 14D:
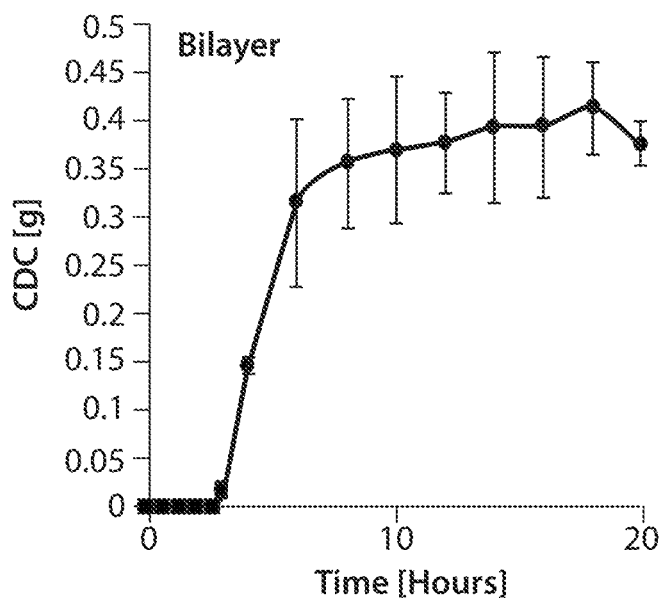
FIG. 14D shows pharmacokinetic evaluation of the bilayer delivery system versus traditional formulations using in vitro and in silico data, according to one set of embodiments.
Figure 14E:
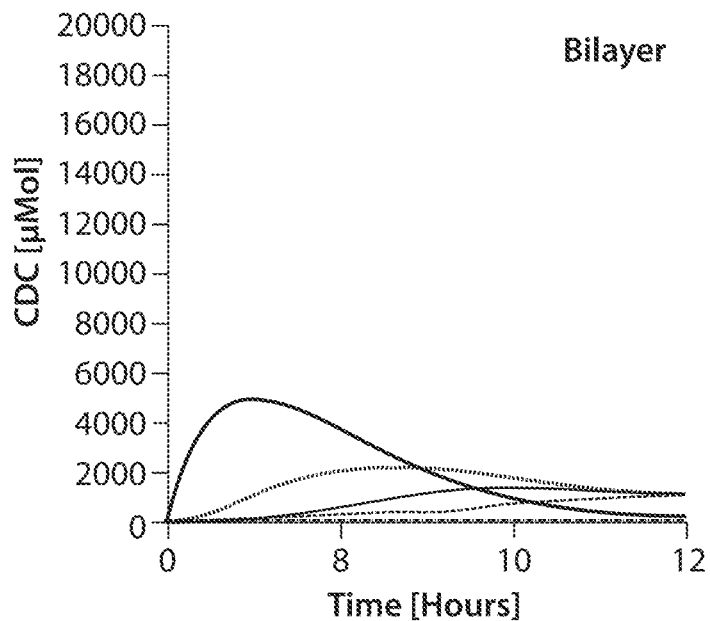
FIG. 14E shows pharmacokinetic evaluation of the bilayer delivery system versus traditional formulations using in vitro and in silico data, according to one set of embodiments.
Figure 14F:
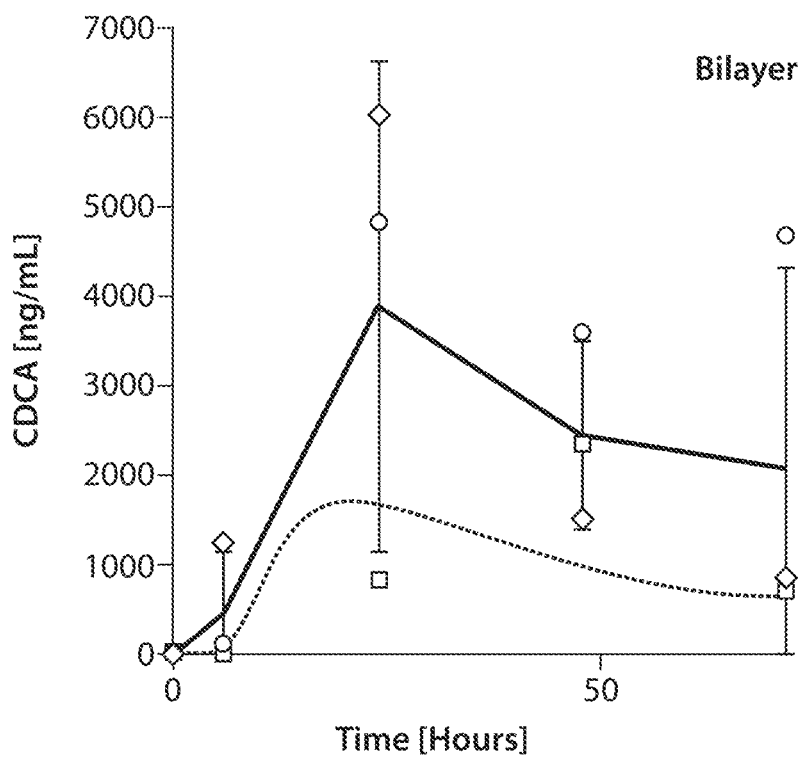
FIG. 14F shows pharmacokinetic evaluation of the bilayer delivery system versus traditional formulations using in vitro and in silico data, according to one set of embodiments.
Figure 14G:
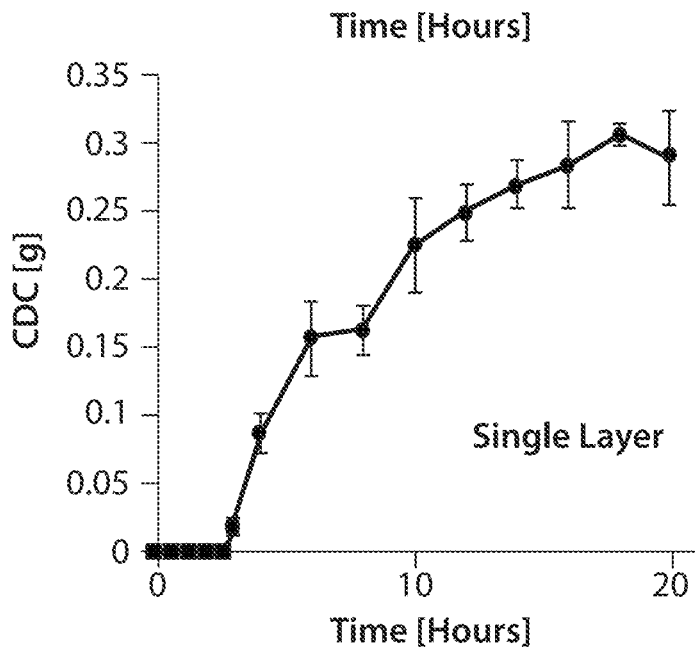
FIG. 14G shows pharmacokinetic evaluation of the bilayer delivery system versus traditional formulations using in vitro and in silico data, according to one set of embodiments.
Figure 14H:
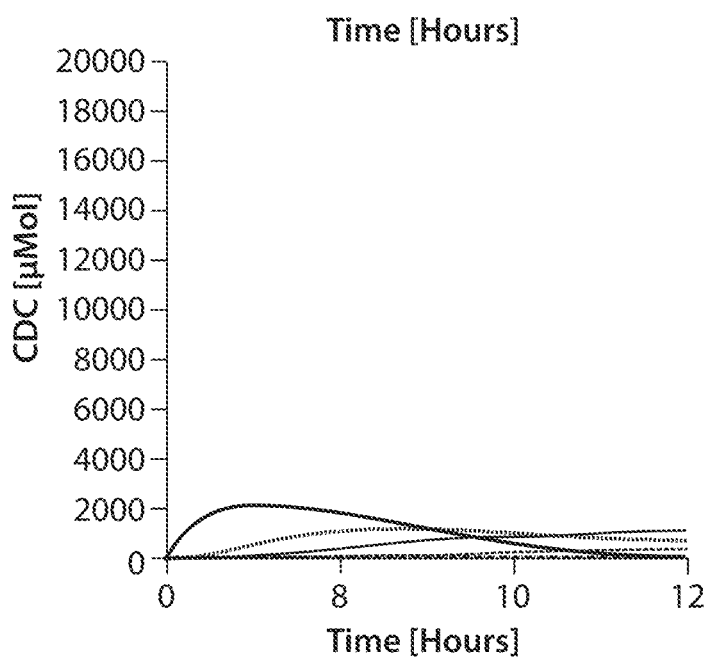
FIG. 14H shows pharmacokinetic evaluation of the bilayer delivery system versus traditional formulations using in vitro and in silico data, according to one set of embodiments.
Figure 14I:
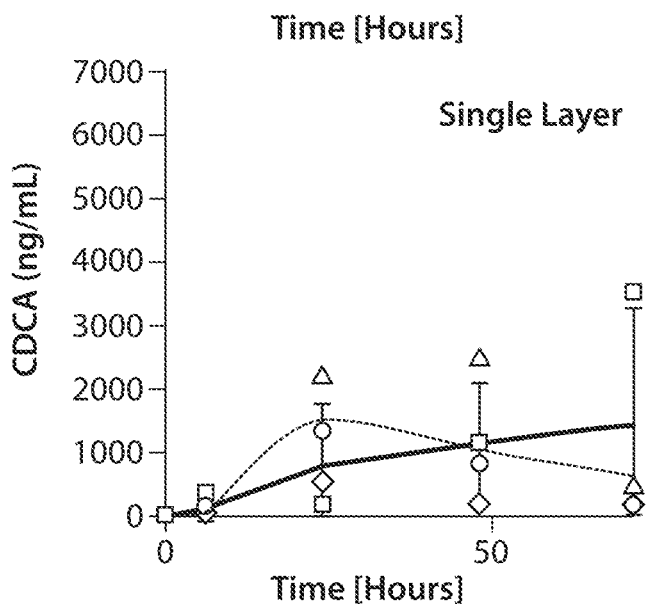
FIG. 14I shows pharmacokinetic evaluation of the bilayer delivery system versus traditional formulations using in vitro and in silico data, according to one set of embodiments.
Figure 14J:
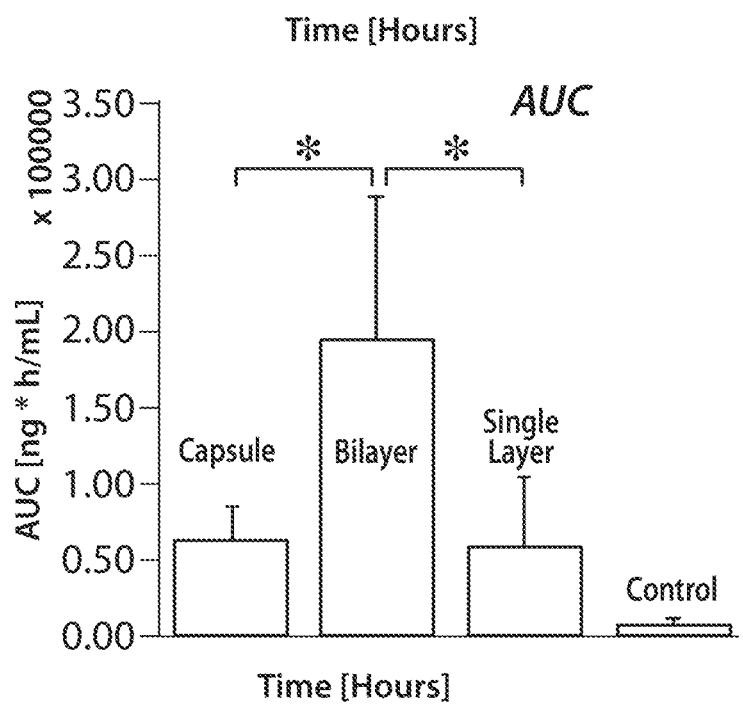
FIG. 14J shows pharmacokinetic evaluation of the bilayer delivery system versus traditional formulations using in vitro and in silico data, according to one set of embodiments.
Figure 14K:
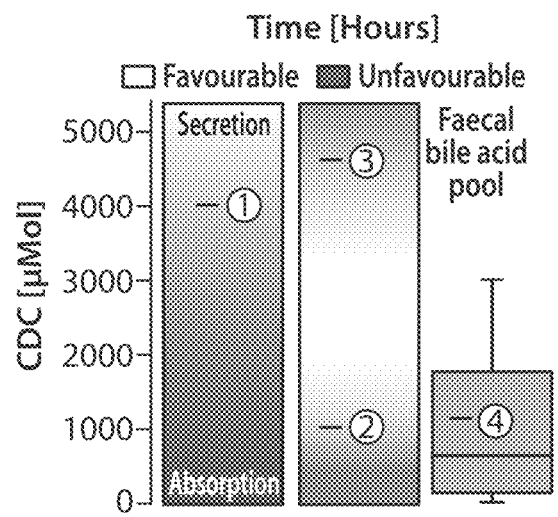
FIG. 14K shows pharmacokinetic evaluation of the bilayer delivery system versus traditional formulations using in vitro and in silico data, according to one set of embodiments.
Figure 14L:
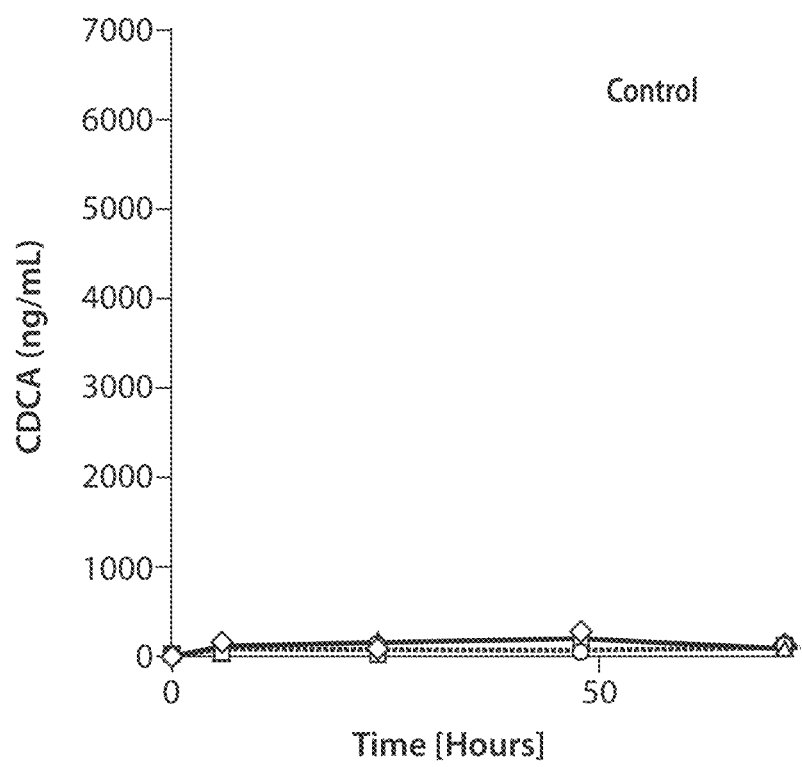
FIG. 14L shows pharmacokinetic evaluation of the bilayer delivery system versus traditional formulations using in vitro and in silico data, according to one set of embodiments.

Assuming first order kinetics and an average bile acid concentration of 2 mM: $K_{abs(0-5)}$ = 0.323 h$^{-1}$
$V_d$ = 25.81 L/Kg (1600 L/62 Kg) Estimated pig weight: 40 Kg
Cl = 25 L/h → $k_{eli}$ = 0.024218939 h$^{-1}$ Following pH triggered disintegration of EUDRAGIT® S100, CDC was immediately and completely released with a half-life of 0.5 hours from the capsule formulation (100 rounds per minute (rpm), FIG. 14A; lag time: 1.5 hours). Under identical conditions, the bilayer system released CDC following first order kinetics with a half-life of approximately 2.5 hours (FIG. 14; lag time: 2 hours). The single layer system, serving as control for a conventional colonic drug delivery system with sustained release kinetics, released CDC with a half-life of approximately 6 hours (FIG. 14G; lag time: 2 hours).

Figure 15A:
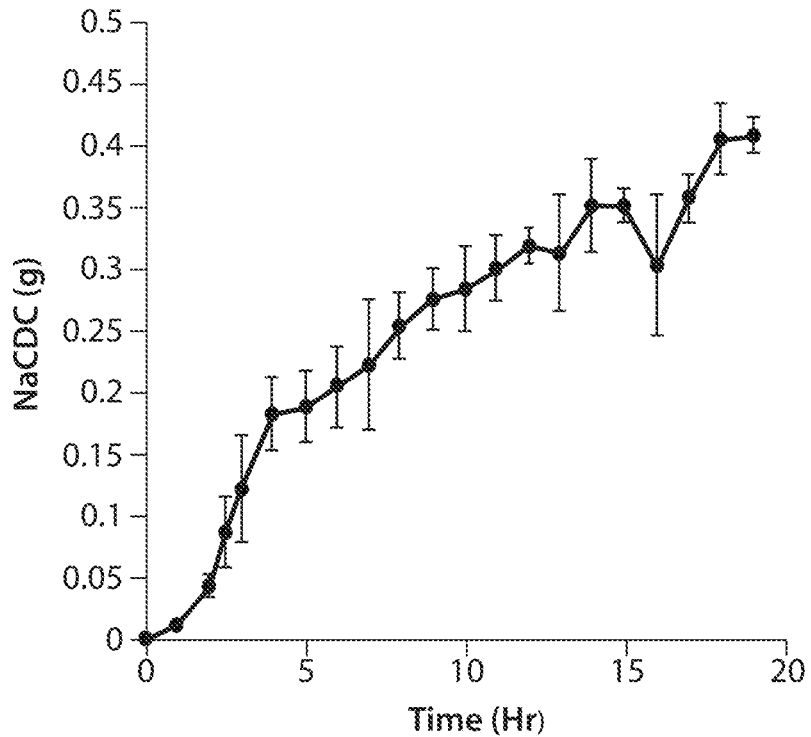
FIG. 15A shows the in vitro release pattern of the bilayer delivery system where release was assessed in Simulated Intestinal Fluid (0.2M, SIF, pH 6.8) for one hour before the pH was adjusted to pH 7.4 (0.2M NaOH, 100 rpm), according to one set of embodiments.
Figure 15B:
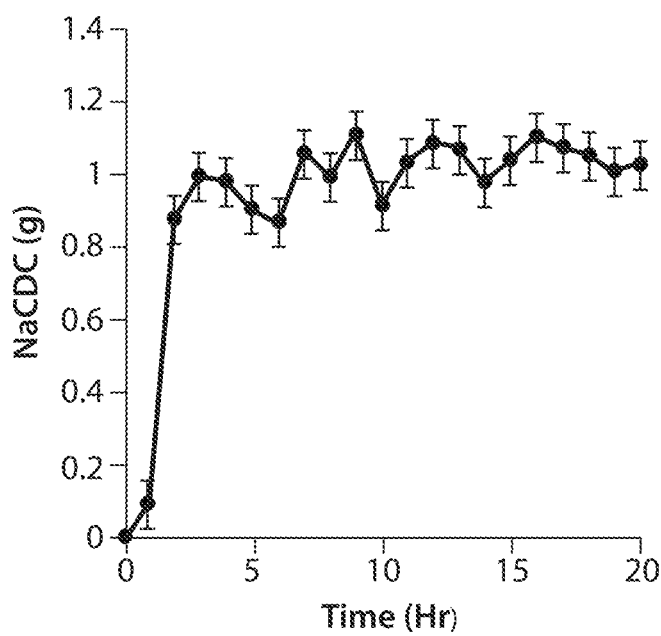
FIG. 15B shows the in vitro release pattern of the capsule formulation where release was assessed in Simulated Intestinal Fluid (0.2M, SIF, pH 6.8) for one hour before the pH was adjusted to pH 7.4 (0.2M NaOH, 100 rpm), according to one set of embodiments.

Importantly, when performing the release experiment at 50 rpm, it was observed that a biphasic release pattern initially releasing ~150 mg CDC within 3 hours after pH triggered disintegration (FIG. 15A). Following first order kinetics, the bilayer tablet released CDC over a course 16 hours thereafter (~80% CDC released). Under identical conditions (e.g., 50 rpm) the capsule formulation released its full payload within 0.5 hours (FIG. 15B).

To better understand local colonic CDC levels, a six-compartment pharmacokinetic in silico model based on physiological characteristics and the in vitro pharmacokinetic profile of the delivery systems. Local colonic peak concentrations of 16.2 (6.2 hours), 5.0 (7 hours), and 2.2 mM (7 hours) were observed for the capsule, for the bilayer and the single layer formulation respectively (FIG. 14B, E and H). Modeled systemic CDC levels reached $C_{max}$ after 19.3 hours (1696 ng/ml), 21.6 hours (1694.7 ng/mL), and 27.45 hours (1477 ng/mL) respectively (FIG. 14C, F and I). In vivo serum CDCA levels following intestinal placement of the delivery systems matched modelled levels, and $C_{max}$ was 1182±296.43 (24 hours), 3895.93±2725.87 (24 hours) and 1409.40±1825.31 (72 hours) for capsule, bilayer and single layer respectively (FIG. 14C, F and I). Control experiments were performed in pigs not receiving CDC. Maximal CDCA levels were 87.36±107.63 in this group (FIG. 14C, F and L).

Pharmacokinetic evaluation of the bilayer delivery system versus traditional formulations are made in FIG. 14. In vitro release pattern of 1 g CDC capsules (FIG. 14A), bilayered delivery systems in FIG. 14D, single layered delivery systems in FIG. 14G (serving as control for a conventional extended release delivery system, exposed to Simulated Gastric Fluid (SGF, 1 h), Simulated Intestinal Fluid (0.2M, SIF, pH 6.8, 1 h) and SIF (0.2M. pH 7.4), respectively (100 rpm)). An in silico pharmacokinetic model was used to understand CDC levels over time in the colon. In FIG. 14B, 1 g CDC capsule are shown, in FIG. 14E, the bilayered delivery system (2x) is used, and in FIG. 14H, the single layered delivery system (2x) is shown. For comparison FIG. 14K shows colonic CDC levels that have previously been linked to secretory, prokinetic, distinct prokinetic effects and are shown in comparison to phycological bile acid levels. The pharmacokinetic model was also used to predict systemic bile acid levels in swine (dashed line) which are shown in comparison to systemic levels (solid lines, LC-MS) for C) 1 g CDC capsules a F) bilayered delivery systems (2x) and I) a single layered delivery system (2x, n=4). Results are depicted as mean of n=3±SD unless otherwise noted (*p≤0.05).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an." as used herein in the specification and in the claims, unless clearly indicated to the contrary, should be understood to mean "at least one."

The phrase "and/or." as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either." "one of," "only one of." or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B." or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Some embodiments may be embodied as a method, of which various examples have been described. The acts performed as part of the methods may be ordered in any suitable way. Accordingly, embodiments may be constructed in which acts are performed in an order different than illustrated, which may include different (e.g., more or less) acts than those that are described, and/or that may involve performing some acts simultaneously, even though the acts are shown as being performed sequentially in the embodiments specifically described above.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An article, comprising:
   a first portion comprising a first bile acid salt, wherein the first portion is an immediate release layer, wherein the first bile acid salt is present in the first portion in an amount greater than or equal to 100 milligrams and less than or equal to 2 grams; and
   a second portion adjacent to the first portion, the second portion comprising a second bile acid salt, wherein the second portion is an extended release layer, wherein the second bile acid salt is present in the second portion in an amount greater than or equal to 100 milligrams and less than or equal to 2 grams,
   wherein the first bile acid salt comprises sodium chenodeoxycholate,
   wherein the second bile acid salt comprises sodium chenodeoxycholate, and
   wherein the first and second bile acid salts are present in different amounts and the total amount of bile acid salt in the first portion and the second portion is greater than or equal to 80 wt % and less than or equal to 98 wt % versus the total weight of the first portion and second portion.

2. The article of claim 1, wherein the article is a pill, tablet, or capsule.

3. The article of claim 2, wherein the article is a tablet.

4. The article of claim 1, wherein the second portion further comprises hydroxypropylmethyl cellulose.

5. The article of claim 1, wherein, upon administration, the first portion fully dissolves within one-fifth of the distance between the ileocecal valve and the hepatic flexure.

6. The article of claim 1, wherein, upon administration of the article, a local colonic concentration of the bile acid salt of in the subject is at least 3 mM.

7. A method comprising orally administering to a subject the article of claim 1.

8. A method of treating a disease, disorder, or condition in a subject comprising administering the article of claim 1 to the subject in need thereof.

9. The method of claim 8, wherein the disease, disorder, or condition is a gastrointestinal disease.

10. The method of claim 8, wherein the subject is suffering from constipation.

11. An article, comprising:
    a first portion comprising a first bile acid salt, wherein the first portion is an immediate release layer, wherein the first bile acid salt is present in the first portion in an amount greater than or equal to 80 wt % and less than or equal to 98 wt % versus the total weight of the first portion; and
    a second portion adjacent to the first portion, the second portion comprising a second bile acid salt, wherein the second portion is an extended release layer, wherein the second bile acid salt is present in the second portion in an amount greater than or equal to 75 wt % and less than or equal to 90 wt % versus the total weight of the second portion,
    wherein the first and second bile acid salts are present in different amounts and the total amount of bile acid salt in the article is greater than or equal to 350 mg and less than or equal to 3 g
    wherein the first bile acid salt comprises sodium chenodeoxycholate, and
    wherein the second bile acid salt comprises sodium chenodeoxycholate.

12. An article, comprising:
    a first layer including a first amount of sodium chenodeoxycholate; and
    a second layer including a second amount of sodium chenodeoxycholate,
    wherein, together, the first amount and the second amount make up greater than or equal to 80 wt % and less than 95 wt % of the total weight of the article.

13. The article of claim 1, further comprising a pH-triggered degradable coating associated with the article.

14. The article of claim 11, further comprising a pH-triggered degradable coating associated with the article.

15. The article of claim 1, wherein the article does not comprise any additional therapeutic agents.

16. The article of claim 11, wherein the article does not comprise any additional therapeutic agents.

17. The article of claim 12, wherein the article does not comprise any additional therapeutic agents.

18. The article of claim 1, wherein the second portion further comprises one or more of hydroxypropyl methylcellulose and magnesium stearate.

19. The article of claim 11, wherein the second portion further comprises one or more of hydroxypropyl methylcellulose and magnesium stearate.

20. The article of claim 12, wherein the second layer further comprises one or more of hydroxypropyl methylcellulose and magnesium stearate.

* * * * *